US012383633B1

(12) United States Patent
Li et al.

(10) Patent No.: US 12,383,633 B1
(45) Date of Patent: Aug. 12, 2025

(54) INJECTABLE FORMULATIONS OF PARP INHIBITORS AND USES THEREOF

(71) Applicant: ZYMERON CORPORATION, Research Triangle Park, NC (US)

(72) Inventors: Xu Li, Research Triangle Park, NC (US); Zhiguo Zhou, Research Triangle Park, NC (US); Krishan Kumar, Research Triangle Park, NC (US); Chunyan Cao, Research Triangle Park, NC (US)

(73) Assignee: ZYMERON CORPORATION, Research Triangle Park, NC (US)

( * ) Notice: Subject to any disclaimer, the term of this patent is extended or adjusted under 35 U.S.C. 154(b) by 0 days.

(21) Appl. No.: 18/903,882

(22) Filed: Oct. 1, 2024

(51) Int. Cl.
A61K 31/502 (2006.01)
A61K 9/00 (2006.01)
A61K 9/19 (2006.01)
A61K 31/4184 (2006.01)
A61K 31/454 (2006.01)
A61K 31/5025 (2006.01)
A61K 31/55 (2006.01)
A61K 47/69 (2017.01)

(52) U.S. Cl.
CPC ........ A61K 47/6951 (2017.08); A61K 9/0019 (2013.01); A61K 9/19 (2013.01); A61K 31/4184 (2013.01); A61K 31/454 (2013.01); A61K 31/502 (2013.01); A61K 31/5025 (2013.01); A61K 31/55 (2013.01)

(58) Field of Classification Search
None
See application file for complete search history.

(56) References Cited

U.S. PATENT DOCUMENTS

| 5,134,127 | A | 7/1992 | Stella et al. | |
|---|---|---|---|---|
| 6,284,269 | B1 | 9/2001 | Struengmann et al. | |
| 8,475,842 | B2 | 7/2013 | Bechtold et al. | |
| 9,200,088 | B2 | 12/2015 | Antle | |
| 11,633,396 | B2 | 4/2023 | Bechtold et al. | |
| 2006/0009517 | A1* | 1/2006 | Webber | A61P 3/10 514/520 |
| 2012/0130144 | A1* | 5/2012 | Sherman | A61K 31/4709 514/378 |
| 2018/0170944 | A1* | 6/2018 | Li | A61K 45/06 |
| 2024/0165073 | A1 | 5/2024 | Moreno | |
| 2024/0165125 | A1 | 5/2024 | Cloyd et al. | |

FOREIGN PATENT DOCUMENTS

| EP | 3184513 A1 | 6/2017 |
|---|---|---|
| WO | 2014161131 A1 | 10/2014 |

OTHER PUBLICATIONS

Ahmad, A., et al. "The clinically used PARP inhibitor olaparib improves organ function, suppresses inflammatory responses and accelerates wound healing in a murine model of third-degree burn injury." British journal of pharmacology 175.2 (2018): 232-245.

Ahmad, A., et al. "The PARP inhibitor olaparib exerts beneficial effects in mice subjected to cecal ligature and puncture and in cells subjected to oxidative stress without impairing DNA integrity: A potential opportunity for repurposing a clinically used oncological drug for the experimental therapy of sepsis." Pharmacological research 145 (2019): 104263.

Friedlander, M. et al. "Managing adverse effects associated with poly (ADP-ribose) polymerase inhibitors in ovarian cancer: a synthesis of clinical trial and real-world data." American Society of Clinical Oncology Educational Book 43 (2023): e390876.

Knight, C. D., et al. "A narrative review of prehospital hemorrhagic shock treatment with non-blood product medications." Transfusion 63 (2023): S256-S262.

Korkmaz-Icöz, S., et al. "Olaparib protects cardiomyocytes against oxidative stress and improves graft contractility during the early phase after heart transplantation in rats." British Journal of Pharmacology 175.2 (2018): 246-261.

Liaudet, L., et al. "Protection Against Hemorrhagic Shock in Mice Genetically Deficient in poly(ADP-Ribose) Polymerase" Proceedings of the National academy of Sciences 2000; 97: 10203-10208.

Ma, D. Q., et al. "New injectable melphalan formulations utilizing (SBE)7m-β-CD or HP-β-CD." International journal of pharmaceutics 189.2 (1999): 227-234.

Miller, R. E. et al. "PARP inhibitors in ovarian cancer: overcoming resistance with combination strategies." Journal of Gynecologic Oncology 33.3: e44 (2022).

Morales, J., et al. "Review of poly (ADP-ribose) polymerase (PARP) mechanisms of action and rationale for targeting in cancer and other diseases." Critical Reviews™ in Eukaryotic Gene Expression 24.1 15-28 (2014).

Ren, L., et al. "Inclusion complex of docetaxel with sulfobutyl ether β-cyclodextrin: preparation, in vitro cytotoxicity and in vivo safety." Polymers 12.10 (2020): 2336.

Skarda, D. E., et al. "Increased poly (ADP-ribose) polymerase activity during porcine hemorrhagic shock is transient and predictive of mortality." Resuscitation 75.1 (2007): 135-144.

Stella, V.J. et al. "Cyclodextrins." Toxicologic pathology 36.1 (2008): 30-42.

Stella, V.J. et al. "Sulfobutylether-β-cyclodextrin." International Journal of Pharmaceutics 583 (2020): 119396.

Szejtli, J. Cyclodextrins in Drug Formulations: Part II, Pharmaceutical Technology, 16-24, 1991.

Vetter, V., et al. "Comprehensive Review on PARP Inhibitors in Ovarian Cancer: A Breakthrough in Diagnostic and Therapeutic Approaches" Health Book TIMES Oncology Hematology 2023; 1: 40-45.

* cited by examiner

Primary Examiner — Jake M Vu
(74) Attorney, Agent, or Firm — Michael Best & Friedrich LLP

(57) ABSTRACT

Described herein are injectable or infusible formulations of PARP inhibitors. In one aspect, the formulation comprises a PARP inhibitor and a cyclodextrin. The injectable or infusible PARP inhibitor-cyclodextrin formulation improves drug solubility, bioavailability, and therapeutic effectiveness. Also described herein are methods for treating oncological and non-oncological indications with injectable or infusible formulations of PARP inhibitors.

14 Claims, 10 Drawing Sheets

INJECTABLE FORMULATIONS OF PARP INHIBITORS AND USES THEREOF

FEDERALLY SPONSORED RESEARCH

This invention was made with government support under contract number HT942523C0067 awarded by the Department of Defense. The government has certain rights in the invention.

BACKGROUND

Poly-(ADP-ribose) polymerase (PARP) is a critical enzyme involved in DNA repair, primarily in the base excision repair pathway. PARP inhibitor therapeutics exploit synthetic lethality, a phenomenon wherein the inhibition of two separate DNA repair pathways leads to the accumulation of DNA damage, culminating in cell death. This concept is particularly pertinent in the context of ovarian cancer, where patients with mutations in the BRCA1 or BRCA2 genes have compromised homologous recombination DNA repair mechanisms, making them highly susceptible to the effects of PARP inhibition. These inhibitors specifically target cancer cells with BRCA mutations, impairing their ability to repair DNA damage and thereby inducing cell death. This approach offers a more precise and effective therapeutic option for patients with BRCA-mutated ovarian cancer, improving response rates and PFS and demonstrating a trend toward prolonged overall survival (OS).

Several PARP inhibitors including olaparib (LYNPARZA®), rucaparib (RUBRACA®), niraparib (ZEJULA®), and talazoparib (TALZENNA®) were developed as oral dosage forms. See FIG. 1. These drugs have been licensed for the treatment of ovarian cancer and are in clinical development for pancreatic cancer and prostate cancer.

The activation of PARP, especially for PARP1 that conducts over 90% of total PARylation activity, has emerged as one of the central mechanisms for systemic inflammation, endothelial dysfunction, peripheral vascular failure, multiple organ dysfunction, and death in hemorrhagic shock. Hemorrhagic shock is responsible for over 35% of prehospital traumatic deaths and over 40% of all deaths within the first 24 hours following injury. Multiple intervention strategies are necessary for prolonged prehospital management and improved casualty survivability including improved blood products, hemostatic, damage control resuscitation, and therapeutic interventions targeting coagulopathy, immune modulation, metabolic, and inflammatory processes. Pharmaceutical interventions near or at the point of injury in prolonged field care military settings are particularly valuable to mitigate or delay the pathophysiologic consequences of hemorrhagic shock, ultimately enabling survival at a higher level of care.

Currently, there are no approved non-oral formulations, e.g., injectable formulations, of PARP inhibitors for oncological indications and non-oncological indications such as hemorrhagic shock or septic shock. Improvement of the water-solubility of these PARP inhibitors is needed for the development of injectable formulations. Thus, there is an unmet need for injectable formulations of PARP inhibitors with high bioavailability and rapid effectiveness.

What is needed are compositions and methods for improving the solubility of PARP inhibitors to generate injectable or infusible formulations of PARP inhibitors for oncological and non-oncological indications.

SUMMARY

One embodiment described herein is a pharmaceutical composition comprising an amorphous powder of an inclusion complex comprising one or more PARP inhibitors and a cyclodextrin (CD) or derivative thereof in in a mass ratio of PARP inhibitor to CD or derivative thereof of about 1:5 to about 1:4800. In one aspect, the PARP inhibitor comprises olaparib, rucaparib, niraparib, veliparib, talazoparib, or combinations thereof. In another aspect, the CD comprises an α-, β-, or γ-cyclodextrin having 6, 7, or 8 α-1,4-linked glucose units. In another aspect, the CD derivative comprises a methyl-β-cyclodextrin, a 2-hydroxypropyl-β-cyclodextrin, a 2-hydroxypropyl-γ-cyclodextrin, or a sulfoalkylether-β-cyclodextrin. In another aspect, the CD derivative comprises sulfobutylether-β-cyclodextrin (SBE-β-CD). In another aspect, the mass ratio of PARP inhibitor to CD or derivative thereof is about 1:27 to about 1:280. In another aspect, the pharmaceutical composition is stable for at least about 3 years at room temperature. In another aspect, the pharmaceutical composition completely dissolves in an aqueous solution in less than about 10 minutes.

Another embodiment described herein is a kit comprising: a pharmaceutical composition described herein; optionally, a diluent or solvent; optionally, injection or infusion materials or devices; and optionally, one or more of packaging, a label, or instructions for use.

Another embodiment described herein is a method of treating, ameliorating, or inhibiting the progress of hemorrhagic shock, septic shock, or cancer in a subject in need thereof, the method comprising: dissolving a pharmaceutical composition described herein with a pharmaceutically acceptable solution for injection or infusion; and administering a therapeutically effective amount of the dissolved pharmaceutical composition to a subject in need thereof by injection or infusion. In one aspect, the dissolved pharmaceutical composition is free of organic solvents.

Another embodiment described herein is a method of treating, ameliorating, or inhibiting the progress of hemorrhagic shock, septic shock, or cancer in a subject in need thereof, the method comprising administering to the subject a therapeutically effective amount of a pharmaceutical composition comprising one or more PARP inhibitors and a cyclodextrin (CD) or derivative thereof in an inclusion complex and in a mass ratio of PARP inhibitor to CD or derivative thereof of about 1:5 to about 1:4800. In one aspect, the pharmaceutical composition is administered to the subject by intravenous, intravascular, intraosseous, intraarterial, intramuscular, subcutaneous, or intraperitoneal injection or infusion. In another aspect, the therapeutically effective amount of the pharmaceutical composition is from about 0.05 mg/kg to about 1.0 mg/kg for hemorrhagic shock; from about 0.1 mg/kg to about 2.0 mg/kg for septic shock; and from about 0.3 mg/kg to about 2.7 mg/kg for cancer. In another aspect, the subject is a mammal selected from a human, horse, cow, pig, sheep, goat, rabbit, dog, or cat.

Another embodiment described herein is a method of making an amorphous powdered pharmaceutical composition, the method comprising: mixing one or more PARP inhibitors with an aqueous solution of a cyclodextrin (CD) or derivative thereof at a mass ratio of about 1:5 to about 1:4800 to create a mixture of the one or more PARP inhibitors and the CD or derivative thereof in an inclusion complex; freezing the mixture at −80° C.; and lyophilizing the frozen mixture to create the amorphous powdered pharmaceutical composition. In one aspect, the one or more PARP inhibitors are an amorphous powder form made by dissolving the one or more PARP inhibitors in a solvent comprising an alcohol and water; freezing the solution at −80° C.; and lyophilizing the frozen solution to create the amorphous powder form of the one or more PARP inhibitors. In another aspect, mixing further comprises one or more of adding water to the mixture, sonicating the mixture, agitating the mixture, or filtering the mixture.

Another embodiment described herein is an injectable or infusible pharmaceutical composition made by a process comprising: mixing one or more PARP inhibitors with an aqueous solution of a cyclodextrin (CD) or derivative thereof at a mass ratio of about 1:5 to about 1:4800 to create a mixture of the one or more PARP inhibitors and the CD or derivative thereof in an inclusion complex; freezing the mixture at −80° C.; lyophilizing the frozen mixture to create an amorphous powdered pharmaceutical composition; and dissolving the amorphous powdered pharmaceutical composition with a pharmaceutically acceptable solution for injection or infusion.

This disclosure provides for other aspects and embodiments that will be apparent in light of the following detailed description and accompanying drawings.

DESCRIPTION OF THE DRAWINGS

FIG. 11A shows an olaparib/β-cyclodextrin phase solubility diagram at 25° C. in water. FIG. 11B shows an olaparib/D-mannitol phase solubility diagram at 25° C. in water.

FIG. 12A shows an olaparib/HP-β-cyclodextrin phase solubility diagram at 25° C. in water. FIG. 12B shows an olaparib/HP-γ-cyclodextrin phase solubility diagram at 25° C. in water.

Figure 1:
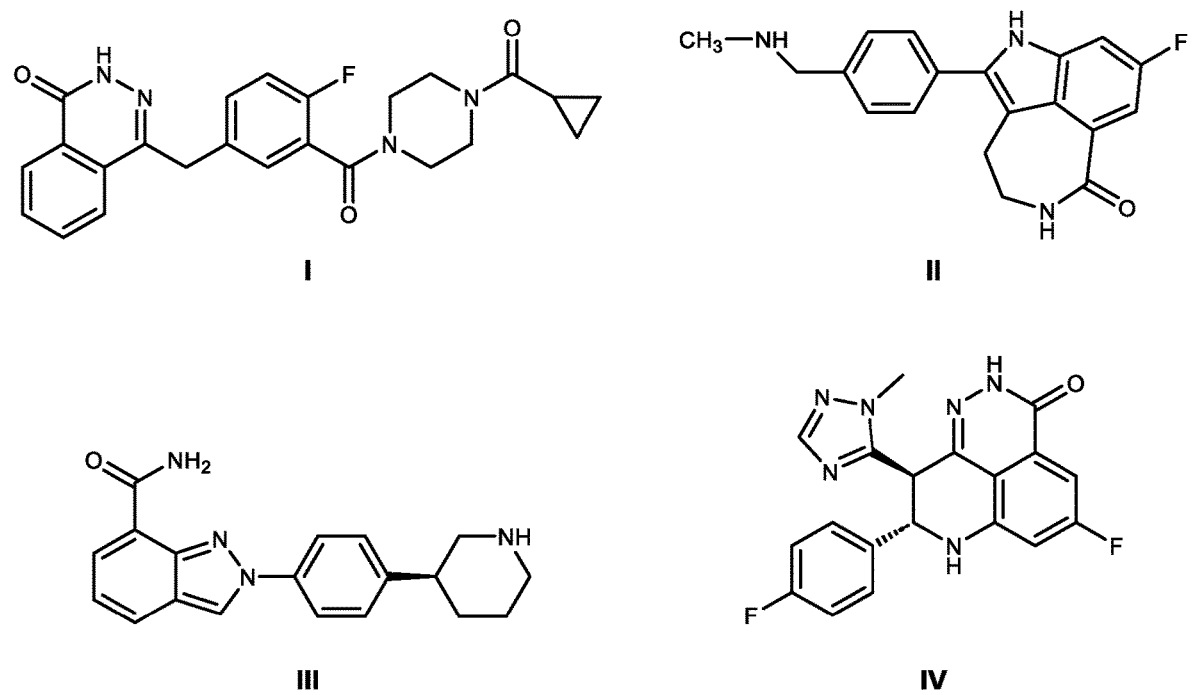
FIG. 1 shows the chemical structures of exemplary PARP inhibitors including (I) olaparib (LYNPARZA®); (II) rucaparib (RUBRACA®); (III) niraparib (ZEJULA®); and (IV) talazoparib (TALZENNA®). Olaparib is a crystalline solid; rucaparib is a camsylate salt; and niraparib and talazoparib are tosylate salts.

Before any embodiments of the disclosure are explained in detail, it is to be understood that the disclosure is not limited in its application to the details of construction and the arrangement of components set forth in the following description or illustrated in the accompanying drawings. Also, it is to be understood that the phraseology and terminology used herein is for the purpose of description and should not be regarded as limiting.

DETAILED DESCRIPTION

Pharmaceutical compositions and methods are described herein for treating, ameliorating, or inhibiting the progress of hemorrhagic or septic shock in a subject. Also described herein are pharmaceutical compositions and methods for treating, ameliorating, or inhibiting the progress of cancer in a subject. The disclosed pharmaceutical compositions are specifically formulated for parenteral administration (e.g., injection or infusion) to subjects. In some embodiments, the pharmaceutical compositions and methods comprise one or more PARP inhibitors and one or more solubilizing excipients. The PARP inhibitor may comprise olaparib, rucaparib, niraparib, veliparib, talazoparib, or combinations thereof. The solubilizing excipient may comprise a sugar-based, water-solubilizing excipient such as a cyclodextrin or derivative thereof. The one or more PARP inhibitors and one or more solubilizing excipients form inclusion complexes in the disclosed pharmaceutical compositions to increase the solubility and bioavailability of the PARP inhibitors in a subject.

In the following description, various embodiments and individual features are disclosed. As will be apparent to a person having ordinary skill in the art, all combinations of such embodiments and features are possible and can result in preferred embodiments.

Definitions

Unless otherwise defined, all technical and scientific terms used herein have the same meaning as commonly understood by one of ordinary skill in the art. For example, any nomenclatures used in connection with, and techniques of biochemistry, molecular biology, immunology, microbiology, genetics, cell and tissue culture, and protein and nucleic acid chemistry described herein are well-known and commonly used in the art. In case of conflict, the present disclosure, including definitions, will control. Exemplary methods and materials are described below, although methods and materials similar or equivalent to those described herein can be used in practice or testing of the embodiments and aspects described herein.

As used herein, terms such as "include," "including," "contain," "containing," "having," and the like mean "comprising." The present disclosure also contemplates other embodiments "comprising," "consisting essentially of," and "consisting of" the embodiments or elements presented herein, whether explicitly set forth or not. As used herein, "comprising," is an "open-ended" term that does not exclude additional, unrecited elements or method steps. As used herein, "consisting essentially of" limits the scope of a claim to the specified materials or steps and those that do not materially affect the basic and novel characteristics of the claimed invention. As used herein, "consisting of" excludes any element, step, or ingredient not specified in the claim.

As used herein, the terms "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "and/or" refers to both the conjunctive and disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points, or as described above in the definition of "about."

As used herein, the terms "room temperature," "RT," or "ambient temperature" refer to the typical temperature in an indoor laboratory setting. In one aspect, the laboratory setting is climate-controlled to maintain the temperature at a substantially uniform temperature or with a specific range of temperatures. In one aspect, "room temperature" refers to a temperature of about 15-30° C., including all integers and endpoints within the specified range. In another aspect, "room temperature" refers a temperature of about 15-30° C.; about 20-30° C.; about 22-30° C.; about 25-30° C.; about 27-30° C.; about 15-22° C.; about 15-25° C.; about 15-27° C.; about 20-22° C.; about 20-25° C.; about 20-27° C.; about 22-25° C.; about 22-27° C.; about 25-27° C.; about 15° C.±10%; about 20° C.±10%; about 22° C.±10%; about 25° C.±10%; about 27° C.±10%; ~ 20° C., ~22° C., ~25° C., or ~27° C., at standard atmospheric pressure.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "dose" denotes any form of an active ingredient formulation or composition, including cells, that contains an amount sufficient to initiate or produce a therapeutic effect with at least one or more administrations. "Formulation" and "composition" are used interchangeably herein.

As used herein, the term "prophylaxis" refers to preventing or reducing the progression of a disorder, either to a statistically significant degree or to a degree detectable by a person of ordinary skill in the art.

As used herein, the terms "effective amount" or "therapeutically effective amount," refer to a substantially non-toxic, but sufficient amount of an action, agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired. In some embodiments, "effective amount" may also refer to a dosage of the compounds or compositions effective for eliciting a desired effect. This term as used herein may also refer to an amount effective at bringing about a desired in vivo effect in an animal, mammal, or human.

As used herein, the term "subject" refers to an animal. Typically, the subject is a mammal. A subject also refers to primates (e.g., humans, male or female; infant, adolescent, or adult), non-human primates (e.g., monkeys, apes, lemurs), rats, mice, rabbits, pigs, cows, sheep, goats, horses, dogs, cats, fish, birds, and the like. In one embodiment, the subject is a primate. In one embodiment, the subject is a human. The methods and compositions disclosed herein can be used on a sample either in vitro (for example, on isolated cells or tissues) or in vivo in a subject (i.e., a living organism, such as a human patient). In some embodiments, the subject comprises a human who is undergoing treatment using a composition and/or method as described herein.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifested.

"Administration" or "administering," as used herein, refers to providing, contacting, and/or delivery of an action, agent, composition, or cell(s) by any appropriate route to achieve a desired effect. In some embodiments, the term "administering" may also refer to the placement of a compound or a composition as disclosed herein into a subject by a method or route that results in at least partial localization of the compound or composition at a desired site in the subject. Administration may include, but is not limited to, oral, sublingual, parenteral (e.g., intravenous, intracardiac, intravascular, infusion (e.g., cardiac catheter infusion), subcutaneous, intraperitoneal, intracutaneous, intramuscular, intraarticular, intraarterial, intrasynovial, intrasternal, intrathecal, intraosseous, intralesional, or intracranial injection), enteral, transdermal, topical, buccal, rectal, vaginal, nasal, ophthalmic, via inhalation, and implants. Via the parenteral route, the compound or composition may be in the form of solutions or suspensions for injection or infusion, or as lyophilized powders. Via the enteral route, the compound or composition may be in the form of capsules, gel capsules, tablets, sugar-coated tablets, syrups, suspensions, solutions, powders, granules, emulsions, or microspheres, nanospheres, lipid vesicles, or polymer vesicles allowing for controlled release. Via the topical route, the compound or composition may be in the form of an aerosol, spray, powder, lotion, cream, paste, gel, ointment, oil, suspensions, solutions, or emulsions.

As used herein, the term "$C_{max}$" refers to the maximum observed blood (plasma, serum, or whole blood) concentration or the maximum blood concentration calculated or estimated from a concentration to time curve and may be expressed in units of mg/L or ng/ml, as applicable.

As used herein, the term "$T_{max}$" refers to the time after administration at which $C_{max}$ occurs and may be expressed in units of hours (hr) or minutes (min), as applicable.

As used herein, "PARP inhibitor" refers to a group of compounds that reduces or abolishes the activity of one or more poly (ADP-ribose) polymerase (PARP) enzymes in a cell, tissue, or subject. PARP enzyme family members, particularly PARP1 and PARP2, play important roles in DNA replication, transcriptional regulation, and DNA damage repair. As disclosed herein, PARP inhibitors and pharmaceutical compositions comprising such PARP inhibitors, can be used to treat, ameliorate, or inhibit the progress of various indications including, but not limited to, hemorrhagic shock, septic shock, and cancer. FIG. 1 shows the chemical structures of exemplary PARP inhibitors including olaparib (LYNPARZA®); rucaparib (RUBRACA®); niraparib (ZEJULA®); and talazoparib (TALZENNA®). Olaparib is a crystalline solid; rucaparib is a camsylate salt; and niraparib and talazoparib are tosylate salts. In certain embodiments described herein, pharmaceutical compositions may comprise one or more PARP inhibitors comprising olaparib (LYNPARZA®), rucaparib (RUBRACA®), niraparib (ZEJULA®), veliparib (ABT-888), talazoparib (TALZENNA®), or combinations thereof.

As used herein, "solubilizing excipient" refers to a compound or agent capable of increasing the solubility of another compound or therapeutic agent, particularly a PARP inhibitor as described herein, in aqueous solution.

As used herein, "inclusion complex" or "inclusion compound" refers to a water-soluble chemical complex structure where one "host" compound encloses (in whole or in part) another "guest" compound within a molecular "cavity" of the host compound. The guest compound is positioned in the host's cavity without significantly altering the host compound's molecular structure. This interaction between the host and guest compounds is purely van der Waals bonding. The inclusion complexation can significantly increase the water solubility and often times, the physio-chemical stability, of the guest compound. Inclusion complexation depends on the relative size of the host compound cavity and the relative size of the guest compound molecule, thus determining the complex stability and the host:guest molecule ratio. In some embodiments, a host compound may include a solubilizing excipient (e.g., cyclodextrin) and a guest compound may include a PARP inhibitor, where the solubilizing excipient wholly or partially encloses the PARP inhibitor in a cavity void of the solubilizing excipient molecule.

As used herein, "hemorrhagic shock" refers to a condition in a subject induced by the loss of a substantial quantity of the subject's total blood volume, resulting in an inadequate flow of blood through vital organs, including the heart and the brain, such that normal physiological organ functioning is compromised. The loss of blood can be caused by trauma, including blunt or penetrating trauma, such as an injury, a deep cut, or a burn, for example, or trauma sustained in the performance of a surgical operation. Substantial blood loss can also occur as a result of non-traumatic bleeding, for example, gastrointestinal bleeding, such as may be caused by, for example, a peptic ulcer or any other gastrointestinal disorder. Substantial blood loss includes the loss of at least 15%, or about 15%, at least 20%, or about 20%, at least 30%, or about 30%, at least 40% or about 40% of the total blood volume of a subject. Hemorrhagic shock can involve the activation of various pro-inflammatory response pathways. Hemorrhagic shock followed by resuscitation (HS/R) causes a systemic inflammatory response and often leads to organ injury and failure. The injury occurring following hemorrhagic shock is unique in that there is a global insult to all organ systems. The inability to meet the cellular metabolic demands results in rapid tissue injury and organ dysfunction.

As used herein, "septic shock" or "sepsis" refers to a clinical disorder having symptoms that can include abnormalities in body temperature, heart rate, breathing rate, white blood cell count, hypertension, organ perfusion abnormalities, and multiple organ failure/dysfunction. Septic shock is particularly characterized by maldistribution of blood flow and disturbances in tissue oxygen in various organs of the body. Distribution of blood flow may become heterogenous with subsequent under- and overperfusion of various tissues. Septic shock patients usually die as a result of poor tissue perfusion and injury followed by multiple organ failure. Septic shock can be caused by bacterial (either gram negative or gram positive), fungal, viral, or other infection. Septic shock is commonly caused by "gram-negative" endotoxin-producing aerobic rods such as *Escherichia coli, Klebsiella pneumoniae, Proteus species, Pseudomonas aeruginosa*, and *Salmonella*. Septic shock involved with gram negative bacteria is referred to as "endotoxic shock." Similar to hemorrhagic shock, septic shock involves the activation of various pro-inflammatory response pathways.

As used herein, "cancer" refers to a disease characterized by the rapid and uncontrolled growth of aberrant cells. Cancer cells can spread locally or through the bloodstream and lymphatic system to other parts of the body. Examples of various cancers include, but are not limited to, breast cancer, prostate cancer, ovarian cancer, fallopian tube cancer, peritoneal cancer, cervical cancer, skin cancer, pancreatic cancer, colorectal cancer, renal or kidney cancer, liver cancer, brain cancer, neck cancer, stomach cancer, esophageal cancer, lymphoma, blood cancer, leukemia, myeloma, lung cancer, and the like. As used herein, "solid tumor cancer" refers to sarcomas, carcinomas, and lymphomas where one or more abnormal tissue masses (i.e., tumors) are formed. "Solid tumor cancer" may also refer to a "non-blood cancer," as commonly known in the art. In certain embodiments of the present disclosure, a subject may be treated with a pharmaceutical composition comprising one or more PARP inhibitors as described herein for a solid tumor cancer having BRCA1/2 gene pathogenic variants or other markers of homologous recombination repair deficiency. For example, these pathogenic BRCA1/2 cancers may include, but are not limited to, ovarian cancer, prostate cancer, breast cancer, or pancreatic cancer.

Pharmaceutical Compounds and Compositions

Described herein are water-soluble, injectable, or infusible pharmaceutical compositions comprising one or more PARP inhibitors in combination with a solubilizing excipient (e.g., a cyclodextrin (CD) or derivative thereof). In some embodiments, the compositions are formulated for intravenous (IV), intraosseous (IO), intramuscular (IM), or subcutaneous (SC) injection or infusion administrations; have enhanced local absorption (i.e., $T_{max}$<10 minutes); and are efficacious for both oncologic applications and non-oncologic applications (e.g., anti-hemorrhagic shock and antiseptic shock indications).

The natural water solubility of PARP inhibitors is low. For example, olaparib (LYNPARZA®) has a water solubility of <0.07 mg/mL. Pure olaparib is a crystalline solid which significantly limits the dissolution and dissolving rates even in some organic solvents such as ethanol (heating-assisted dissolving). Rucaparib (RUBRACAR) has a water solubility around 1 mg/mL across the physiological pH range. The difference is that rucaparib has a free secondary amine, which improves its water solubility, particularly for the camsylate salt form. The FDA-approved solid oral formulations of PARP inhibitors, e.g., olaparib (LYNPARZA®), are thus not suitable for emergency medicine applications in certain settings (e.g., military combat) due to their low bioavailability and relatively slow absorption rate ($T_{max}$ of 1.5 hr in healthy patients), which may be further delayed in cases of massive hemorrhage. The compositions disclosed herein provide water-soluble, injectable, or infusible PARP inhibitor formulations that are more suitable for clinical and field use against indications including hemorrhagic shock, septic shock, and cancer. In certain non-limiting exemplary embodiments, the disclosed formulations can enhance the solubility of PARP inhibitors almost 100-fold.

In some embodiments, one or more solubilizing excipients form an inclusion complex with one or more PARP inhibitors to increase the solubility of the PARP inhibitors in the disclosed pharmaceutical compositions. In one aspect, the disclosed pharmaceutical compositions comprise a sugar-based, water-solubilizing excipient that includes but is not limited to, mannitol, cyclodextrins, or cyclodextrin derivatives thereof. The term "cyclodextrin," as used herein, relates to both cyclodextrins and cyclodextrin derivatives, including, for example, the cyclodextrin derivatives described herein.

Figure 2A:
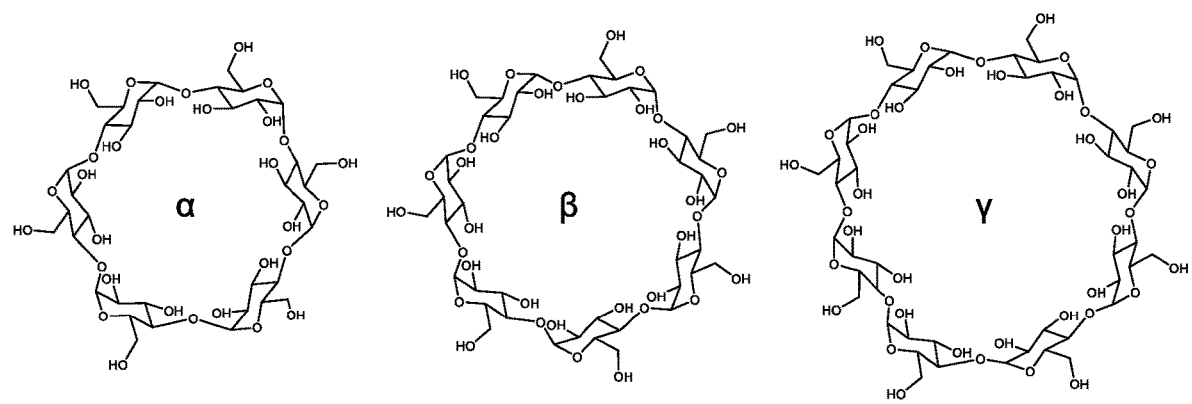
FIG. 2A-B show the chemical structures of α-, β-, γ-cyclodextrins (FIG. 2A), and sulfobutylether-β-cyclodextrins (FIG. 2B). α-, β-, γ-cyclodextrins contain 6, 7, or 8 glucopyranose units, respectively. Sulfobutylether-β-cyclodextrins are modified derivatives of β-cyclodextrins that have between 6 and 7 sulfobutylether moieties per molecule (approximately 1 per glucopyranose moiety).
Figure 2B:
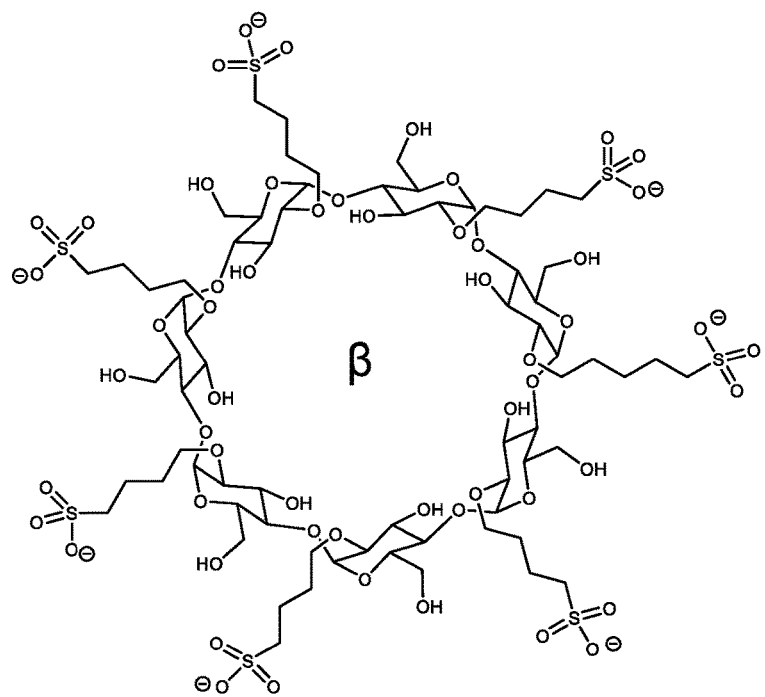

Cyclodextrins, also known as cyclomyloses, cycloglucans, and Schardinger dextrins, are naturally occurring clathrates obtained, for example, from the action of *Bacillus macerans* amylase on starch to form homogenous cyclic α-1,4-linked glucopyranose units. Cyclodextrins are cyclic oligosaccharides with hydroxyl groups on the outer surface and a void cavity in the center. Their outer surface is hydrophilic and therefore they are usually soluble in water, but the cavity has a hydrophobic character. The most common cyclodextrins are α-, β-, and γ-cyclodextrins that contain 6, 7, or 8 α-1,4-linked glucose units, respectively, which determines the cavity size (FIG. 2A). The α-, β-, and γ-cyclodextrins containing 6, 7, or 8 α-1,4-linked glucose units have molecular weights of 972.84, 1134.98, and 1297.12 g/mol, respectively. Cyclodextrins have hydrophobic cavities that are able to form inclusion complexes with other compounds in the solid state or in aqueous solutions. α-, β-, and γ-cyclodextrins have limited aqueous solubility and may show toxicity when given by injection. Therefore, cyclodextrin structures are generally modified to generate a parenterally safe cyclodextrin derivative. A range of cyclodextrin derivatives are known, for example, where one or more of the primary and/or secondary pendant hydroxy (—OH) groups have been derivatized, for example, to form ether groups (e.g., dimethyl ether; hydroxyethyl ether; 2-hydroxypropyl ether; carboxymethyl ether; carboxyethyl ether; glucosyl ether; maltosyl ether; sulfoalkyl ether). The modifications are typically made at one or more of the 2-, 3-, or 6-position hydroxyls. In one aspect, the solubilizing excipient may comprise a cyclodextrin derivative selected from methyl-substituted cyclodextrins, ethyl-substituted cyclodextrins, hydroxyalkyl substituted cyclodextrins, including 2-hydroxypropyl-β-cyclodextrin and 2-hydroxypropyl-γ-cyclodextrin, alkyl ether cyclodextrins, branched cyclodextrins, cationic cyclodextrins, quaternary ammonium cyclodextrins, anionic cyclodextrins, amphoteric cyclodextrins, sulfoalkyl ether β-cyclodextrins, or a modified form thereof, and mixtures thereof. In another aspect, the solubilizing excipient may comprise a cyclodextrin derivative selected from a methyl-β-cyclodextrin, a 2-hydroxypropyl-β-cyclodextrin, a 2-hydroxypropyl-γ-cyclodextrin, or a sulfoalkylether-β-cyclodextrin (e.g., sulfobutylether-β-cyclodextrin (SBE-β-CD)). FIG. 2A-B show the chemical structures of α-, β-, γ-cyclodextrins (FIG. 2A), and a sulfobutylether-β-cyclodextrin derivative (FIG. 2B).

Sulfobutylether-β-cyclodextrins (SBE-β-CDs) are modified derivatives of β-cyclodextrins that have between 6 and 7 sulfobutylether moieties per molecule (approximately 1 per glucopyranose moiety). These sulfobutylether derivatives of β-cyclodextrin have sulfonic acid moieties, with very low pKa values, and carry multiple negative charges at physiological pH values. The four-carbon butyl chain coupled with the repulsion of the end group negative charges allows for an "extension" of the cyclodextrin cavity which results in stronger binding to drug candidates that may not be achieved using other original and modified cyclodextrins. It also provides a potential for ionic charge interactions between the cyclodextrin and a positively charged drug molecule.

Other FDA approved cyclodextrin and cyclodextrin derivative excipients include β-cyclodextrin (BETADEX), hydroxypropyl-β-cyclodextrin (HYDROXYPROPYL BETADEX, HP-β-cyclodextrin), and hydroxypropyl-γ-cyclodextrin (HP-γ-cyclodextrin).

Sulfobutylether-β-cyclodextrin is an FDA-approved excipient (BETADEX SULFOBUTYL ETHER SODIUM) for intravenous and intramuscular injections with 833 mg and 19200 mg, respectively, maximum daily exposure limits. In one non-limiting exemplary aspect described herein, the sulfobutylether-β-cyclodextrin is Captisol® (CyDex Pharmaceuticals). Captisol® sulfobutylether-β-cyclodextrins have an average of 6.5 sulfobutylether moieties per cyclodextrin molecule (e.g., between 6 and 7 sulfobutylether groups) (FIG. 2B).

Sulfobutylether-β-cyclodextrin forms ionic and inclusion complexes with many types of drugs. Complexation can significantly increase the solubility and often times, the physio-chemical stability of the drug. Inclusion complexation depends on the relative size of the cyclodextrin cavity and the size of the drug molecule, thus determining the complex stability and the cyclodextrin to drug molecule ratio. Each pair of cyclodextrin and drug molecule requires comprehensive evaluations to determine if and how stable an inclusion complex may be formed. Complexation has also been used to improve dissolution and bioavailability, reduce volatility, allow incorporation of liquids into solid formulations, and reduce unpleasant side effects such as taste and irritation caused by drug contact with tissues, e.g. extravasation at injection sites and GI irritation.

Cyclodextrins and their derivatives such as HP-β-cyclodextrin, HP-γ-cyclodextrin, and SBE-β-CDs are capable of forming inclusion complexes with a wide variety of hydrophobic molecules by taking up a whole molecule (a "guest molecule"), or some part of it, into the cavity void. The stability of the resulting inclusion complex depends on how well the guest molecule fits into the cyclodextrin cavity. In certain embodiments, a solubilizing excipient comprising a cyclodextrin or cyclodextrin derivative is chosen so as to form water-soluble inclusion complexes with one or more PARP inhibitors that can be utilized in an injectable or infusible pharmaceutical composition. In certain embodiments, the formed complexes are stable in water and, once the pharmaceutical composition is delivered to a subject via injection or infusion, the PARP inhibitors are displaced from the cyclodextrin or cyclodextrin derivative molecule to deliver a desired pharmacological and physiological response.

In some embodiments, the pharmaceutical compositions described herein may comprise a stable PARP inhibitor-cyclodextrin inclusion complex that has enhanced water solubility compared to the non-complexed active pharmaceutical ingredient (API) PARP inhibitor. This results in an injectable or infusible formulation that is completely and immediately available in the bloodstream, which does not occur with oral dosage forms. The injectable or infusible formulations disclosed herein can thus be administered to subjects suffering from hemorrhagic shock in, for example, combat settings because the formulation has rapid local tissue absorption (i.e., $T_{max}$<10 minutes) upon IV administration. In comparison, oral dosage forms of PARP inhibitors are not suitable in a combat setting because of the relatively slow absorption rate ($T_{max}$ of 1.5 h).

As discussed above, certain PARP inhibitors, such as pure olaparib, are a crystalline solid which significantly limits the dissolution and dissolving rates even in some organic solvents such as ethanol (heating-assisted dissolving). Therefore, in some aspects disclosed herein, the preparation of an amorphous (i.e., non-crystalline) powder of a PARP inhibitor can help facilitate rapid dissolution in appropriate solvents, in combination with solubilizing excipients as described herein.

In some embodiments, the disclosed pharmaceutical compositions are made by mixing one or more PARP inhibitors with an aqueous solution of a solubilizing excipient at a mass ratio of about 1:5 to about 1:4800 to create a mixture of the one or more PARP inhibitors and the solubilizing excipient in an inclusion complex; freezing the mixture at −80° C.; and lyophilizing the frozen mixture to create an amorphous powdered pharmaceutical composition. In some aspects, the one or more PARP inhibitors are in an amorphous powder form for mixing with the aqueous solution of the solubilizing excipient. In one aspect, this amorphous powder of the one or more PARP inhibitors can be made by dissolving the one or more PARP inhibitors in a solvent comprising an alcohol and water; freezing the solution at −80° C.; and lyophilizing the frozen solution to create the amorphous powder form of the one or more PARP inhibitors which can then be mixed with the aqueous solution of the solubilizing excipient. The amorphous powdered pharmaceutical composition can then be dissolved in an appropriate and pharmaceutically acceptable solution or solvent (e.g., water, saline) for injection or infusion into a subject.

In some embodiments, the disclosed pharmaceutical compositions may be formulated with one or more pharmaceutically acceptable carriers, salts, adjuvants, excipients, diluents, fillers, buffers, stabilizers, preservatives, lubricants, or other materials well-known to those skilled in the art, and optionally other therapeutic or prophylactic agents.

Pharmaceutical excipients useful for the compositions as described herein may comprise: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives s (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, ascorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, oxide); complexing agents black or blends, ferric (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); thickening agents (gelatin having a bloom strength of 50-100); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein. See Remington's Essentials of Pharmaceutics, Pharmaceutical Press Publishing Company, London, UK, $1^{st}$ Edition, 2013, and the Handbook of Pharmaceutical Excipients, 8th Edition, Pharmaceutical Press Publishing Company London, U K, 2017, each of which is incorporated by reference herein for such teachings.

In some embodiments, the disclosed pharmaceutical compositions, when in aqueous solution form, are completely free of, or essentially free of, of any organic solvents and/or preservatives. As used herein, the term "essentially free of" generally means an amount that is less than about 1.0% by weight, or less than about 0.75% by weight, such as less than about 0.5% by weight, less than about 0.25% by weight, less than about 0.1% by weight, less than about 0.05% by weight, less than about 0.01% by weight, less than about 0.005% by weight, less than about 0.001% by weight, less than about 0.0005% by weight, or less than about 0.0001% by weight of the total pharmaceutical composition.

In some embodiments, the disclosed pharmaceutical compositions may comprise one or more PARP inhibitors and one or more solubilizing excipients in a mass ratio of about 1:5 to about 1:4800, including each integer and fraction within this specified range. In other embodiments, the disclosed pharmaceutical compositions may comprise one or more PARP inhibitors and one or more solubilizing excipients in a mass ratio of about 1:10 to about 1:1000, including each integer and fraction within this specified range. For example, in some non-limiting exemplary embodiments, the disclosed pharmaceutical compositions may comprise one or more PARP inhibitors and one or more solubilizing excipients in a mass ratio of about 1:27 to about 1:280. In yet other embodiments, the mass ratio is from about 1:5 to about 1:100, including each integer and fraction within this specified range. In certain non-limiting exemplary embodiments, the mass ratio of the one or more PARP inhibitors to the one or more solubilizing excipients may be about 1:5, about 1:10, about 1:20, about 1:30, about 1:40, about 1:50, about 1:60, about 1:70, about 1:80, about 1:90, about 1:100, about 1:125, about 1:150, about 1:175, about 1:200, about 1:225, about 1:250, about 1:275, or about 1:280, including each integer and fraction between these specific values. In some embodiments, the disclosed pharmaceutical compositions may comprise one or more PARP inhibitors and a cyclodextrin (CD) or derivative thereof in an inclusion complex and in a mass ratio of PARP inhibitor to CD or derivative thereof of about 1:5 to about 1:4800.

In some embodiments, the disclosed pharmaceutical compositions, when in aqueous solution form, may comprise one or more PARP inhibitors and one or more solubilizing excipients in a concentration ranging from about 5-30% (w/v), including each integer and fraction within this specified range. For example, the one or more PARP inhibitors and one or more solubilizing excipients may comprise a concentration of about 5%, 8%, 10%, 12%, 15%, 18%, 20%, 22%, 25%, 28%, or 30%, or about 5-8%, 5-10%, 5-12%, 5-15%, 5-18%, 5-20%, 5-22%, 5-25%, 5-28%, 8-10%, 8-12%, 8-15%, 8-18%, 8-20%, 8-22%, 8-25%, 8-28%, 8-30%, 10-12%, 10-15%, 10-18%, 10-20%, 10-22%, 10-25%, 10-28%, 10-30%, 12-15%, 12-18%, 12-20%, 12-22%, 12-25%, 12-28%, 12-30%, 15-18%, 15-20%, 15-22%, 15-25%, 15-28%, 15-30%, 18-20%, 18-22%, 18-25%, 18-28%, 18-30%, 20-22%, 20-25%, 20-28%, 20-30%, 22-25%, 22-28%, 22-30%, 25-28%, 25-30%, or 28-30% (w/v) of the total pharmaceutical composition, including each integer and fraction within these specified values and ranges.

Methods of Treatment

This disclosure further relates to methods of treating, ameliorating, or inhibiting the progress of hemorrhagic shock, septic shock, or cancer in a subject. The methods comprise administering to the subject a therapeutically effective amount of a pharmaceutical composition comprising one or more PARP inhibitors and one or more solubilizing excipients as described herein.

Mice genetically deficient in PARP undergoing hemorrhagic shock were previously found to be protected from the rapid decrease in blood pressure after liquid resuscitation (maintaining >40 mm Hg blood pressure for >120 min versus <40 min for wild-type mice) and showed a significantly improved survival time (277 min versus 149 min) with diminished multiple organ damage (e.g., 3-fold reduction of gut permeability), when compared to mice with normal PARP activities. In a porcine hemorrhagic shock model, the PARP activity levels in tissues (e.g., muscle and liver) were above 2-fold higher during hemorrhagic shock in non-survivors compared to survivors, indicating that PARP could be a part of initial pathways leading from hemorrhagic shock to death. Multiple organ failure is characterized by septic shock, which involves similar proinflammatory pathways to hemorrhagic shock. Furthermore, PARP inhibitors are known to be effective in treating different types of cancer, particularly cancers having BRCA1/2 gene pathogenic variants or other markers of homologous recombination repair deficiency. Thus, the pharmaceutical compositions described herein comprising one or more PARP inhibitors and one or more solubilizing excipients are administered to subjects in need of treatment to effectively treat, ameliorate, or inhibit the progress of hemorrhagic shock, septic shock, or cancer.

The disclosed pharmaceutical compositions are specifically formulated for parenteral administration (e.g., injection or infusion) to treat, ameliorate, or inhibit the progress of hemorrhagic shock, septic shock, or cancer in a subject. In one aspect, the pharmaceutical composition is administered to the subject by intravenous, intravascular, intraosseous, intraarterial, intramuscular, subcutaneous, or intraperitoneal injection or infusion. In another aspect, the pharmaceutical composition has an absorption $T_{max}$ in the subject of less than about 10 minutes following administration. In another aspect, the pharmaceutical composition is completely cleared from the blood of the subject in less than about 4 hours following administration. In another aspect, the subject is a mammal. In another aspect, the subject is a human, horse, cow, pig, sheep, goat, rabbit, dog, or cat.

In some embodiments, a subject being administered an injectable pharmaceutical composition as described herein may have, or be at risk of developing, one or more of impaired gastrointestinal (GI) drug absorption, small bowel obstruction, extensive peritoneal disease or preexisting refractory nausea, or severe GI tract adverse effects including nausea and vomiting, reduced appetite, dysgeusia constipation, diarrhea, abdominal pain, and/or symptoms of reflux.

In some embodiments, the disclosed pharmaceutical compositions and methods may further comprise administration with other therapeutically active compounds or compositions which are usually applied in the treatment of the oncologic applications and non-oncologic applications disclosed herein, including one or more of hemorrhagic shock, septic shock, or cancer. For example, in the treatment of cancer, the pharmaceutical compositions and methods disclosed herein may be combined with one or more chemotherapeutic drugs or other anti-cancer interventions (e.g., radiation, surgery). The other therapeutically active compounds or compositions can be administered by a route and in an amount commonly used therefore, contemporaneously, or sequentially with the disclosed pharmaceutical compositions. If a pharmaceutical composition described herein and an additional therapeutic agent(s) are not administered simultaneously or essentially simultaneously, then the initial order of administration of the pharmaceutical composition, and the additional therapeutic agent(s), may be varied. Thus, for example, a pharmaceutical composition described herein may be administered first followed by the administration of the additional therapeutic agent(s); or the additional therapeutic agent(s) may be administered first followed by the administration of a pharmaceutical composition described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject.

Dosages and Modes of Administration

In the methods of treatment described herein, the disclosed pharmaceutical compositions can be administered in dosages and by techniques well known to those skilled in the medical and pharmaceutical arts taking into consideration such factors as the age, sex, weight, and condition of the particular subject, and the route of administration.

It will be appreciated that appropriate dosages of the pharmaceutical compositions comprising active PARP inhibitor compounds can vary from patient to patient and can vary based on the particular indication being treated (e.g., oncological versus non-oncological conditions). Determining the optimal dosage will generally involve the balancing of the level of therapeutic benefit against any risk or deleterious side effects of the treatments described herein.

The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound or composition and the route of administration will ultimately be at the discretion of a trained physician, although generally, the dosage will be to achieve local concentrations at the site of action which achieve the desired effect without causing substantial harmful or deleterious side-effects. The actual dosage can also depend on the determined experimental effectiveness of the specific compound or composition that is administered. For example, the dosage may be determined based on in vitro responsiveness of relevant cultured cells, or in vivo responses observed in appropriate animal models or human studies.

For example, a therapeutically effective amount of the disclosed pharmaceutical compositions comprising one or more PARP inhibitors may range from about 0.1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

In certain non-limiting exemplary embodiments described herein, a therapeutically effective amount of the disclosed pharmaceutical compositions may be from about 0.05 mg/kg to about 1.0 mg/kg for hemorrhagic shock; from about 0.1 mg/kg to about 2.0 mg/kg for septic shock; or from about 0.3 mg/kg to about 2.7 mg/kg for cancer.

Administration in vivo can be provided in one or more doses, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In some embodiments, a subject may be administered a single dose of the disclosed pharmaceutical agents, compounds, or compositions. In other embodiments, a subject may be administered a plurality of doses over a period of time. For example, in various non-limiting exemplary embodiments, a pharmaceutical compound or composition as described herein may be administered to a subject once a day (SID/QD), twice a day (BID), three times a day (TID), four times a day (QID), or more, so as to administer a therapeutically effective amount to the subject, where the therapeutically effective amount is any one or more of the doses described herein. In some embodiments, a compound or composition as described herein is administered to a subject 1-3 times per day, 1-7 times per week, 1-9 times per month, 1-12 times per year, or more. In other embodiments, a pharmaceutical compound or composition as described herein is administered for about 1-10 days, 10-20 days, 20-30 days, 30-40 days, 40-50 days, 50-60 days, 60-70 days, 70-80 days, 80-90 days, 90-100 days, 1-6 months, 6-12 months, 1-5 years, or more. In various embodiments, a pharmaceutical compound or composition as described herein is administered at a dose of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, 900-1000 mg/kg, or a combination thereof.

In general, a suitable dose of the pharmaceutical compositions described herein may be in the range of about 1 mg to about 250 mg, or about 100 mg to about 250 mg, per kilogram body weight of the subject per day.

As disclosed herein, the pharmaceutical compositions described herein comprising one or more PARP inhibitors and one or more solubilizing excipients allow for parenteral administration to a subject. The term "parenteral," as used herein, can refer to modes of administration that include, but are not limited to, intravenous, intravascular, intraosseous, intraarterial, intramuscular, subcutaneous, or intraperitoneal injection or infusion. The disclosed formulations suitable for parenteral administration can include aqueous and nonaqueous isotonic, pyrogen-free, sterile injection solutions which may contain anti-oxidants, buffers, stabilizers, bacteriostats, and solutes that render the formulation isotonic with the blood of the intended subject recipient; and aqueous and non-aqueous sterile suspensions which may include suspending agents and thickening agents, and liposomes or other microparticulate systems which are designed to target a PARP inhibitor compound to specific blood components or one or more organs. Examples of suitable isotonic vehicles for use in such formulations include Sodium Chloride Injection, Ringer's Solution, or Lactated Ringer's Injection. The formulations may be presented in unit-dose or multi-dose sealed containers, for example, ampoules and vials, and may be stored in a freeze-dried (lyophilized) condition requiring only the addition of the sterile liquid carrier, for example, water for injections, immediately prior to use.

Methods for Manufacturing

In some embodiments, this disclosure relates to methods for manufacturing a pharmaceutical composition. In one embodiment, a method for making an amorphous powder of the active pharmaceutical ingredient (API) is described. In one embodiment, the API is solubilized in a solvent comprising an alcohol (e.g., ethanol or butanol) and water and the API solvent mixture is stirred to facilitate dissolution. The API solvent mixture is frozen solid (e.g., at −20° C. or −80° C.) and lyophilized. The lyophilization process may contain multiple temperatures and time periods. For example, the frozen API solvent mixture may be lyophilized using a stepped temperature gradient such as −30° C. for 24 h; −10° C. for 32 h; 5° C. for 24 h; 15° C. for 24 h; and 30° C. for 48 hr. The lyophilization may contain additional steps at temperatures from −80° C. to 40° C. for periods of 1 hr to 48 hr. The resulting amorphous API powder can be stored or used for the preparation of an inclusion complex.

In another embodiment, a method for making an amorphous powder of the API and one or more solubilizing excipients is described. In one embodiment, an amorphous powder of the API is created as described herein. In another embodiment a crystalline solid or salt form of the API is dissolved in a solvent. The solvent may contain an alcohol (e.g., ethanol or butanol) or other organic solvent to facilitate the dissolution of the API. In either case, either the amorphous powder of the API or the solubilized API is mixed with a solution of one or more solubilizing excipients. The mixture is stirred, optionally sonicated, and filtered. The filtrate is frozen solid (e.g., at −20° C. or −80° C.) and lyophilized. The lyophilization process may contain multiple temperatures and time periods. For example, the frozen API solvent mixture may be lyophilized using a stepped temperature gradient such as −30° C. for 24 h; −10° C. for 32 h; 5° C. for 24 h; 15° C. for 24 h; and 30° C. for 48 hr. The lyophilization may contain additional steps at temperatures from −80° C. to 40° C. for periods of 1 hr to 48 hr. The resulting amorphous powder of the API and one or more solubilizing excipients may be stored at room temperature, refrigerated, or frozen (e.g., at −20° C. or −80° C.). Alternatively, the amorphous powder of the API and one or more solubilizing excipients may be dissolved in sterile water for injection and dispensed into vials for injection.

Kits

In some embodiments, this disclosure further relates to kits comprising any of the compounds or pharmaceutical compositions disclosed herein and, optionally, one or more of a diluent or solvent, injection or infusion materials or devices, or one or more of packaging, a label, or instructions for use. In certain embodiments, the use of the disclosed kits will treat, ameliorate, or inhibit the progress of hemorrhagic shock, septic shock, or cancer in a subject. The information and instructions of the disclosed kits may be in the form of words, pictures, or both, and the like. In addition, or in the alternative, the disclosed kits may provide information and instructions for methods of administering any one of the compounds or pharmaceutical compositions disclosed herein to a subject, preferably with the benefit of treating, ameliorating, or inhibiting the progress of hemorrhagic shock, septic shock, or cancer in the subject. In some embodiments, the disclosed kits may comprise additional components necessary or appropriate for military combat or clinical settings.

Embodiments

One embodiment described herein is a pharmaceutical composition comprising an amorphous powder of an inclusion complex comprising one or more PARP inhibitors and a cyclodextrin (CD) or derivative thereof in in a mass ratio of PARP inhibitor to CD or derivative thereof of about 1:5 to about 1:4800. In one aspect, the PARP inhibitor comprises olaparib, rucaparib, niraparib, veliparib, talazoparib, or combinations thereof. In another aspect, the CD comprises an α-, β-, or γ-cyclodextrin having 6, 7, or 8 α-1,4-linked glucose units. In another aspect, the CD derivative comprises a methyl-β-cyclodextrin, a 2-hydroxypropyl-β-cyclodextrin, a 2-hydroxypropyl-γ-cyclodextrin, or a sulfoalkylether-β-cyclodextrin. In another aspect, the CD derivative comprises sulfobutylether-β-cyclodextrin (SBE-β-CD). In another aspect, the mass ratio of PARP inhibitor to CD or derivative thereof is about 1:27 to about 1:280. In another aspect, the pharmaceutical composition is stable for at least about 3 years at room temperature. In another aspect, the pharmaceutical composition completely dissolves in an aqueous solution in less than about 10 minutes.

Another embodiment described herein is a kit comprising: a pharmaceutical composition described herein; optionally, a diluent or solvent; optionally, injection or infusion materials or devices; and optionally, one or more of packaging, a label, or instructions for use.

Another embodiment described herein is a method of treating, ameliorating, or inhibiting the progress of hemorrhagic shock, septic shock, or cancer in a subject in need thereof, the method comprising: dissolving a pharmaceutical composition described herein with a pharmaceutically acceptable solution for injection or infusion; and administering a therapeutically effective amount of the dissolved pharmaceutical composition to a subject in need thereof by injection or infusion. In one aspect, the dissolved pharmaceutical composition is free of organic solvents.

Another embodiment described herein is a method of treating, ameliorating, or inhibiting the progress of hemorrhagic shock, septic shock, or cancer in a subject in need thereof, the method comprising administering to the subject a therapeutically effective amount of a pharmaceutical composition comprising one or more PARP inhibitors and a cyclodextrin (CD) or derivative thereof in an inclusion complex and in a mass ratio of PARP inhibitor to CD or derivative thereof of about 1:5 to about 1:4800. In one aspect, the pharmaceutical composition is administered to the subject by intravenous, intravascular, intraosseous, intraarterial, intramuscular, subcutaneous, or intraperitoneal injection or infusion. In another aspect, the therapeutically effective amount of the pharmaceutical composition is from about 0.05 mg/kg to about 1.0 mg/kg for hemorrhagic shock; from about 0.1 mg/kg to about 2.0 mg/kg for septic shock; and from about 0.3 mg/kg to about 2.7 mg/kg for cancer. In another aspect, the subject is a mammal selected from a human, horse, cow, pig, sheep, goat, rabbit, dog, or cat.

Another embodiment described herein is a method of making an amorphous powdered pharmaceutical composition, the method comprising: mixing one or more PARP inhibitors with an aqueous solution of a cyclodextrin (CD) or derivative thereof at a mass ratio of about 1:5 to about 1:4800 to create a mixture of the one or more PARP inhibitors and the CD or derivative thereof in an inclusion complex; freezing the mixture at −80° C.; and lyophilizing the frozen mixture to create the amorphous powdered pharmaceutical composition. In one aspect, the one or more PARP inhibitors are an amorphous powder form made by dissolving the one or more PARP inhibitors in a solvent comprising an alcohol and water; freezing the solution at −80° C.; and lyophilizing the frozen solution to create the amorphous powder form of the one or more PARP inhibitors. In another aspect, mixing further comprises one or more of adding water to the mixture, sonicating the mixture, agitating the mixture, or filtering the mixture.

Another embodiment described herein is an injectable or infusible pharmaceutical composition made by a process comprising: mixing one or more PARP inhibitors with an aqueous solution of a cyclodextrin (CD) or derivative thereof at a mass ratio of about 1:5 to about 1:4800 to create a mixture of the one or more PARP inhibitors and the CD or derivative thereof in an inclusion complex; freezing the mixture at −80° C.; lyophilizing the frozen mixture to create an amorphous powdered pharmaceutical composition; and dissolving the amorphous powdered pharmaceutical composition with a pharmaceutically acceptable solution for injection or infusion.

Another embodiment described herein is a pharmaceutical composition for treating, ameliorating, or inhibiting the progress of hemorrhagic shock, septic shock, or cancer in a subject, the pharmaceutical composition comprising one or more PARP inhibitors and one or more solubilizing excipients. In one aspect, the pharmaceutical composition is formulated for injection or infusion into the subject. In another aspect, the PARP inhibitor comprises olaparib, rucaparib, niraparib, veliparib, talazoparib, or combinations thereof. In another aspect, the solubilizing excipient comprises a sugar-based, water-solubilizing excipient. In another aspect, the solubilizing excipient comprises a cyclodextrin or derivative thereof. In another aspect, the solubilizing excipient comprises an α-, β-, or γ-cyclodextrin having 6, 7, or 8 α-1,4-linked glucose units. In another aspect, the solubilizing excipient comprises a cyclodextrin derivative selected from a methyl-cyclodextrin, a 2-hydroxypropyl-cyclodextrin, or a sulfoalkylether-β-cyclodextrin. In another aspect, the solubilizing excipient comprises sulfobutylether-β-cyclodextrin (SBE-β-CD). In another aspect, the solubilizing excipient comprises 2-hydroxypropyl-β-cyclodextrin (HP-β-CD). In another aspect, the one or more PARP inhibitors and the one or more solubilizing excipients are in the form of an inclusion complex in the pharmaceutical composition. In another aspect, the one or more PARP inhibitors and the one or more solubilizing excipients are present in a mass ratio of about 1:5 to about 1:1000. In another aspect, the one or more PARP inhibitors and the one or more solubilizing excipients are present in a mass ratio of about 1:5 to about 1:100. In another aspect, the pharmaceutical composition is free of organic solvents or preservatives. In another aspect, the one or more PARP inhibitors have at least twice the bioavailability in the subject as compared to a PARP inhibitor in an oral composition that does not include a solubilizing excipient. In another aspect, the pharmaceutical composition is a lyophilized powder form. In another aspect, the lyophilized powder form of the pharmaceutical composition is stable for at least about 3 years at room temperature. In another aspect, the lyophilized powder form of the pharmaceutical composition completely dissolves in an aqueous solution in less than about 10 minutes.

Another embodiment described herein is a kit comprising: a pharmaceutical composition described herein; optionally, a diluent or solvent; optionally, injection or infusion materials or devices; and optionally, one or more of packaging, a label, or instructions for use.

Another embodiment described herein is the use of a pharmaceutical composition described herein as a medicament for treating, ameliorating, or inhibiting the progress of hemorrhagic shock, septic shock, or cancer in a subject.

Another embodiment described herein is a method of treating, ameliorating, or inhibiting the progress of hemorrhagic shock, septic shock, or cancer in a subject, the method comprising administering to the subject a therapeutically effective amount of a pharmaceutical composition comprising one or more PARP inhibitors and one or more solubilizing excipients. In one aspect, the pharmaceutical composition is administered to the subject by intravenous, intravascular, intraosseous, intraarterial, intramuscular, subcutaneous, or intraperitoneal injection or infusion. In another aspect, the therapeutically effective amount of the pharmaceutical composition is from about 0.05 mg/kg to about 1.0 mg/kg for hemorrhagic shock; from about 0.1 mg/kg to about 2.0 mg/kg for septic shock; and from about 0.3 mg/kg to about 2.7 mg/kg for cancer. In another aspect, the pharmaceutical composition is administered to the subject by intravenous injection or infusion and has an absorption $T_{max}$ in the subject of less than about 10 minutes following administration. In another aspect, the pharmaceutical composition is administered to the subject by intravenous injection or infusion and is completely cleared from the blood of the subject in less than about 4 hours following administration. In another aspect, the subject is a mammal. In another aspect, the subject is a human, horse, cow, pig, sheep, goat, rabbit, dog, or cat.

Another embodiment described herein is a method of making a pharmaceutical composition comprising one or more PARP inhibitors and one or more solubilizing excipients for treating, ameliorating, or inhibiting the progress of hemorrhagic shock, septic shock, or cancer in a subject, the method comprising: mixing one or more PARP inhibitors with an aqueous solution of one or more solubilizing excipients to generate a mixture of the one or more PARP inhibitors and the one or more solubilizing excipients. In one aspect, an amorphous powder of the one or more PARP inhibitors is made by dissolving the one or more PARP inhibitors in a solvent comprising an alcohol and water; freezing the solution at −80° C.; and lyophilizing the frozen solution to create an amorphous powder. In another aspect, mixing comprises a period of time of about 30 minutes to about 3 hours at room temperature. In another aspect the method further comprises adding water to the mixture. In another aspect the method further comprises one or more of sonicating, agitating, filtering, freezing, or lyophilizing the mixture. In another aspect, the one or more PARP inhibitors and the one or more solubilizing excipients form an inclusion complex upon mixing. In another aspect, the one or more PARP inhibitors and the one or more solubilizing excipients are mixed at a mass ratio of about 1:5 to about 1:100.

Another embodiment described herein is a pharmaceutical composition comprising one or more PARP inhibitors and one or more solubilizing excipients for treating, ameliorating, or inhibiting the progress of hemorrhagic shock, septic shock, or cancer in a subject, the pharmaceutical composition made by a process comprising: mixing one or more PARP inhibitors with an aqueous solution of one or more solubilizing excipients to generate a mixture of the one or more PARP inhibitors and the one or more solubilizing excipients. In one aspect, an amorphous powder of the one or more PARP inhibitors is made by dissolving the one or more PARP inhibitors in a solvent comprising an alcohol and water; freezing the solution at −80° C.; and lyophilizing the frozen solution to create an amorphous powder. In another aspect, mixing comprises a period of time of about 30 minutes to about 3 hours at room temperature. In another aspect, the process further comprises adding water to the mixture. In another aspect, the process further comprises one or more of sonicating, agitating, filtering, freezing, or lyophilizing the mixture. In another aspect, the one or more PARP inhibitors and the one or more solubilizing excipients form an inclusion complex upon mixing. In another aspect, the one or more PARP inhibitors and the one or more solubilizing excipients are mixed at a mass ratio of about 1:5 to about 1:100.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. A pharmaceutical composition comprising an amorphous powder of an inclusion complex comprising one or more PARP inhibitors and a cyclodextrin (CD) or derivative thereof in in a mass ratio of PARP inhibitor to CD or derivative thereof of about 1:5 to about 1:4800.

Clause 2. The pharmaceutical composition of clause 1, wherein the PARP inhibitor comprises olaparib, rucaparib, niraparib, veliparib, talazoparib, or combinations thereof.

Clause 3. The pharmaceutical composition of clause 1 or 2, wherein the CD comprises an α-, β-, or γ-cyclodextrin having 6, 7, or 8 α-1,4-linked glucose units.

Clause 4. The pharmaceutical composition of any one of clauses 1-3, wherein the CD derivative comprises a methyl-β-cyclodextrin, a 2-hydroxypropyl-β-cyclodextrin, a 2-hydroxypropyl-γ-cyclodextrin, or a sulfoalkylether-β-cyclodextrin.

Clause 5. The pharmaceutical composition of any one of clauses 1-4, wherein the CD derivative comprises sulfobutylether-β-cyclodextrin (SBE-β-CD).

Clause 6. The pharmaceutical composition of any one of clauses 1-5, wherein the mass ratio of PARP inhibitor to CD or derivative thereof is about 1:27 to about 1:280.

Clause 7. The pharmaceutical composition of any one of clauses 1-6, wherein the pharmaceutical composition is stable for at least about 3 years at room temperature.

Clause 8. The pharmaceutical composition of any one of clauses 1-7, wherein the pharmaceutical composition completely dissolves in an aqueous solution in less than about 10 minutes.

Clause 9. A kit comprising:
the pharmaceutical composition of any one of clauses 1-8;
optionally, a diluent or solvent;
optionally, injection or infusion materials or devices; and
optionally, one or more of packaging, a label, or instructions for use.

Clause 10. A method of treating, ameliorating, or inhibiting the progress of hemorrhagic shock, septic shock, or cancer in a subject in need thereof, the method comprising:
dissolving the pharmaceutical composition of any one of clauses 1-8 with a pharmaceutically acceptable solution for injection or infusion; and
administering a therapeutically effective amount of the dissolved pharmaceutical composition to a subject in need thereof by injection or infusion.

Clause 11. The method of clause 10, wherein the dissolved pharmaceutical composition is free of organic solvents.

Clause 12. A method of treating, ameliorating, or inhibiting the progress of hemorrhagic shock, septic shock, or cancer in a subject in need thereof, the method comprising administering to the subject a therapeutically effective amount of a pharmaceutical composition comprising one or more PARP inhibitors and a cyclodextrin (CD) or derivative thereof in an inclusion complex and in a mass ratio of PARP inhibitor to CD or derivative thereof of about 1:5 to about 1:4800.

Clause 13. The method of clause 12, wherein the pharmaceutical composition is administered to the subject by intravenous, intravascular, intraosseous, intraarterial, intramuscular, subcutaneous, or intraperitoneal injection or infusion.

Clause 14. The method of clause 12 or 13, wherein the therapeutically effective amount of the pharmaceutical composition is from about 0.05 mg/kg to about 1.0 mg/kg for hemorrhagic shock; from about 0.1 mg/kg to about 2.0 mg/kg for septic shock; and from about 0.3 mg/kg to about 2.7 mg/kg for cancer.

Clause 15. The method of any one of clauses 12-14, wherein the subject is a mammal selected from a human, horse, cow, pig, sheep, goat, rabbit, dog, or cat.

Clause 16. A method of making an amorphous powdered pharmaceutical composition, the method comprising:
mixing one or more PARP inhibitors with an aqueous solution of a cyclodextrin (CD) or derivative thereof at a mass ratio of about 1:5 to about 1:4800 to create a mixture of the one or more PARP inhibitors and the CD or derivative thereof in an inclusion complex;
freezing the mixture at −80° C.; and
lyophilizing the frozen mixture to create the amorphous powdered pharmaceutical composition.

Clause 17. The method of clause 16, wherein the one or more PARP inhibitors are an amorphous powder form made by dissolving the one or more PARP inhibitors in a solvent comprising an alcohol and water; freezing the solution at −80° C.; and lyophilizing the frozen solution to create the amorphous powder form of the one or more PARP inhibitors.

Clause 18. The method of clause 16 or 17, wherein mixing further comprises one or more of adding water to the mixture, sonicating the mixture, agitating the mixture, or filtering the mixture.

Clause 19. An injectable or infusible pharmaceutical composition made by a process comprising:
mixing one or more PARP inhibitors with an aqueous solution of a cyclodextrin (CD) or derivative thereof at a mass ratio of about 1:5 to about 1:4800 to create a mixture of the one or more PARP inhibitors and the CD or derivative thereof in an inclusion complex;
freezing the mixture at −80° C.;
lyophilizing the frozen mixture to create an amorphous powdered pharmaceutical composition; and
dissolving the amorphous powdered pharmaceutical composition with a pharmaceutically acceptable solution for injection or infusion.

EXAMPLES

Example 1

Preparation of Amorphous Powder of Olaparib

For preparation of the amorphous powder of olaparib, 800 mL of t-butanol was heated to 45° C. to liquefy and then 200 mL of sterile water was added. 1 gram of crystal olaparib was then added under sonication and stirring at room temperature until completely dissolved after about 1 hour.

The homogeneous solution was frozen at −80° C. for 2 hours and then lyophilized under 0.03 mbar to obtain an amorphous powder of olaparib.

Alternatively, 40 mL of 75% ethanol was added into 400 mg of crystal olaparib under sonication and stirring until the solid was completely dissolved after about 30 min. Next, additional sterile water was added to dilute to less than 20% of ethanol. The homogeneous solution was frozen at −80° C. for 2 hours and then lyophilized under 0.03 mbar to obtain an amorphous powder of olaparib. Lyophilization conditions are shown in Table 1.

TABLE 1

Olaparib Lyophilization Process Conditions

| Step | Temperature | Time |
| --- | --- | --- |
| 1 | −30° C. | 24 hr |
| 2 | −10° C. | 32 hr |
| 3 | 5° C. | 24 hr |
| 4 | 15° C. | 24 hr |
| 5 | 30° C. | 48 hr |

Example 2

Preparation of Amorphous Powder of Olaparib Injectable Formulation

Figure 3A:
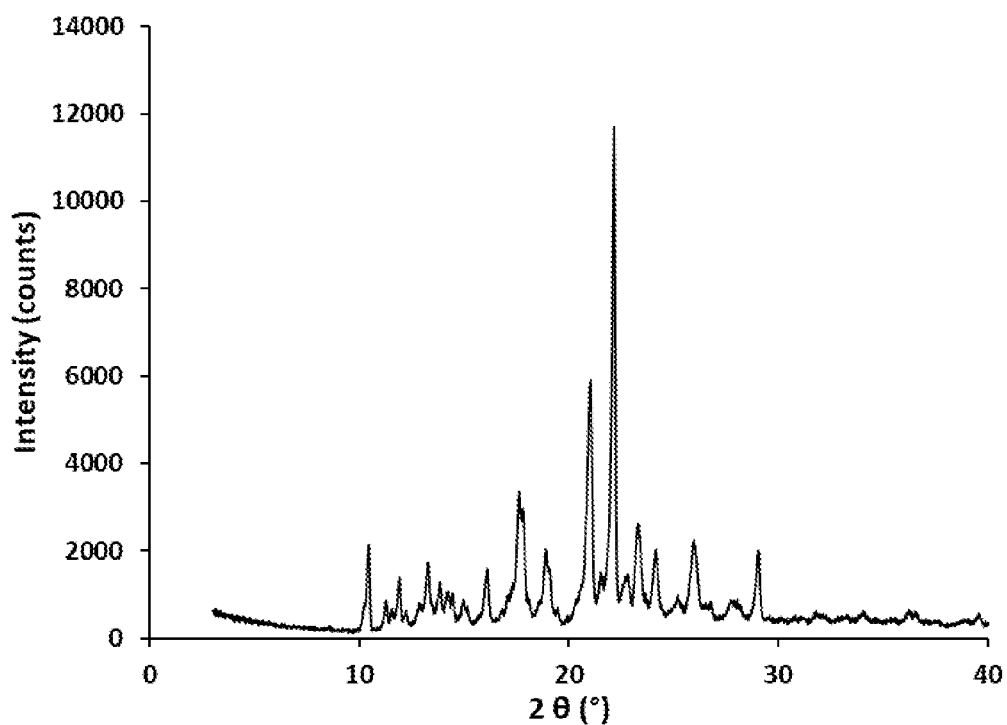
FIG. 3A-C show X-ray powder diffraction (XRPD) spectra of crystalline olaparib (FIG. 3A), lyophilized amorphous olaparib (FIG. 3B), and lyophilized amorphous olaparib-sulfobutylether-β-cyclodextrin inclusion complex (FIG. 3C).
Figure 3B:
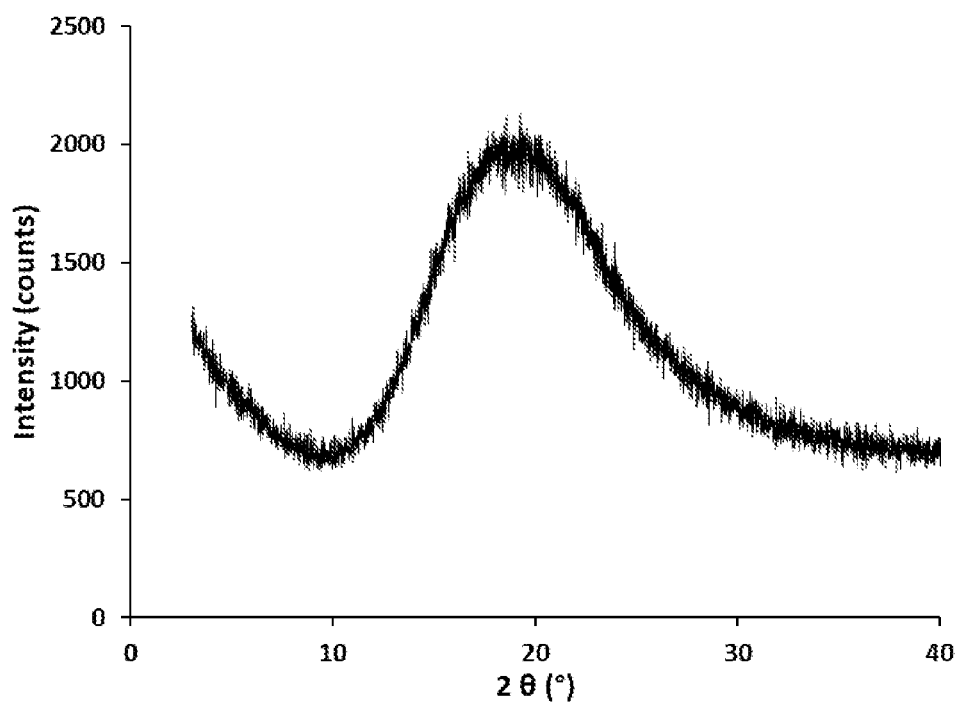
Figure 3C:
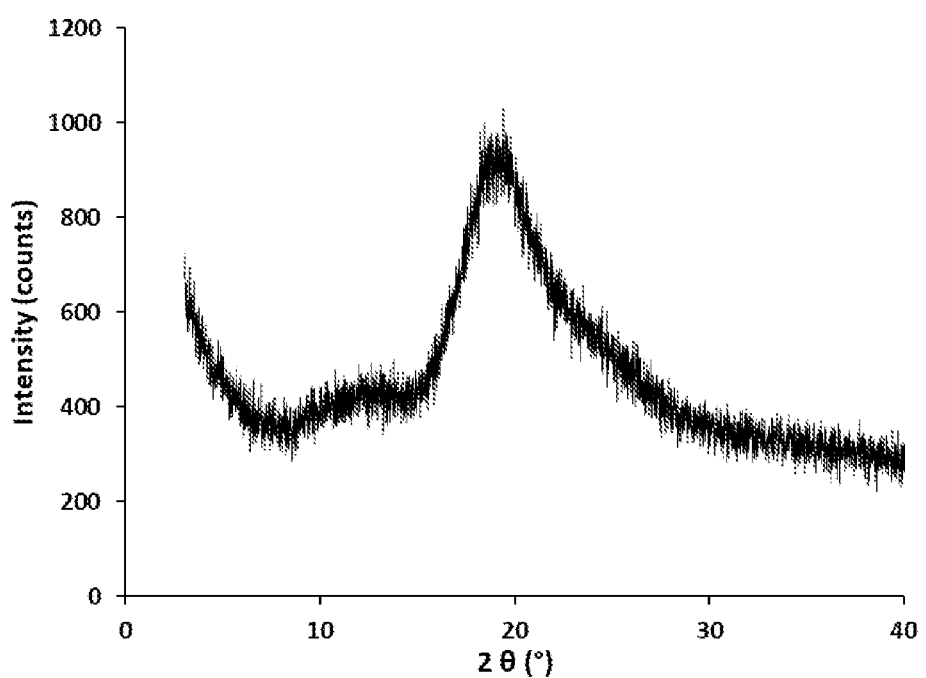

For the preparation of the olaparib-sulfobutylether-β-cyclodextrin inclusion complex, an aqueous solution of sulfobutylether-β-cyclodextrin (around 40%, w/v) containing 30 grams of sulfobutylether-β-cyclodextrin was mixed with 500 mg olaparib amorphous powder, sonicated, and shaken at room temperature for 2 hr. Additional sterile water was added under vortexing at 1,000 RPM. The mixture was then filtered with a 0.22 μm PES membrane, and the resultant homogeneous solution having 5 mg/mL olaparib was frozen at −80° C. for two hours, then lyophilized under 0.03 mbar to obtain a lyophilized powder of olaparib-sulfobutylether-β-cyclodextrin inclusion complex. FIG. 3C shows the XRD pattern of the lyophilized, amorphous powder of olaparib-sulfobutylether-β-cyclodextrin inclusion complex.

Alternatively, 500 mg of crystal olaparib was mixed in 50 mL of 75% ethanol and sonicated and stirred until completely dissolved. To prepare sulfobutylether-β-cyclodextrin solution, 200 mL of sterile water was added to 30 grams of sulfobutylether-β-cyclodextrin under shaking, and subsequently the olaparib ethanol solution was added under stirring to obtain a homogeneous solution. The mixture was filtered with a 0.22 μm PES membrane. The filtered solution was frozen at −80° C. for two hours, then lyophilized under 0.03 mbar to obtain lyophilized amorphous powder of olaparib-sulfobutylether-β-cyclodextrin. Lyophilization conditions are shown in Table 2.

TABLE 2

Olaparib-Sulfobutylether-β-Cyclodextrin Lyophilization Process Conditions

| Step | Temperature | Time |
| --- | --- | --- |
| 1 | −30° C. | 24 hr |
| 2 | −10° C. | 32 hr |
| 3 | 5° C. | 24 hr |
| 4 | 15° C. | 24 hr |
| 5 | 30° C. | 48 hr |

Example 3

Dissolution of Lyophilized Powder Injectable Formulation of Olaparib

Figure 4:
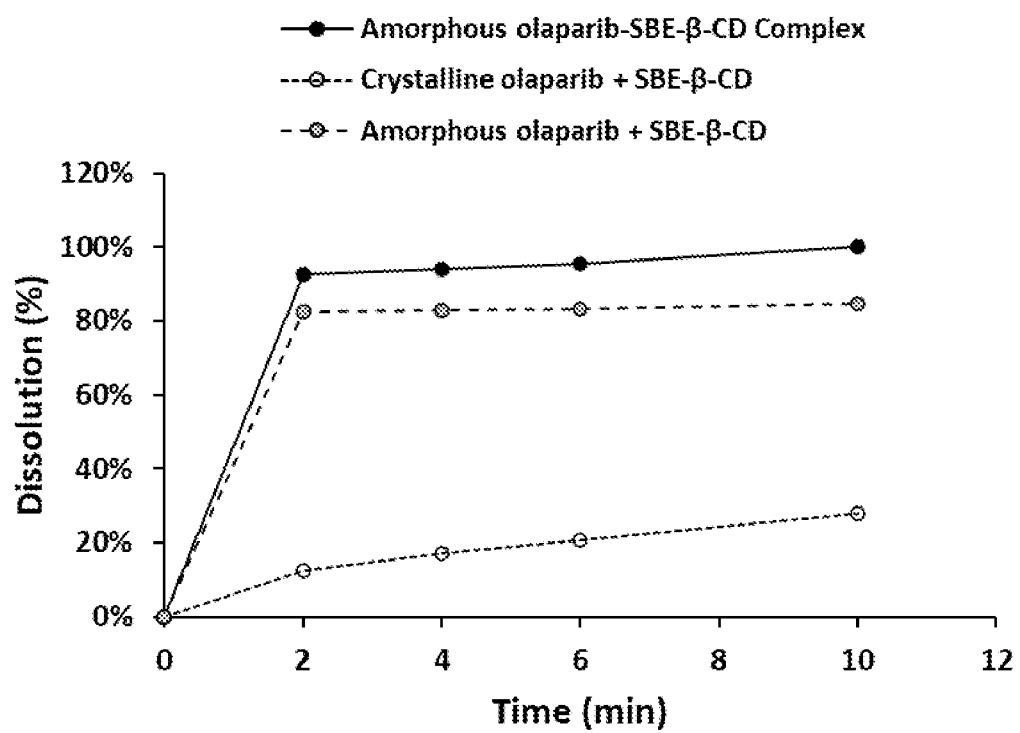
FIG. 4 shows the rapid dissolution of olaparib-sulfobutylether-β-cyclodextrin inclusion complex (>95% dissolved within 2 min).

The quantity of dissolved olaparib depended on its complexation with the solubilizer sulfobutylether-β-cyclodextrin, which was influenced by several parameters including the mass ratio of olaparib-to-sulfobutylether-β-cyclodextrin, the incubation temperature, and time. FIG. 4 shows the percent dissolution of olaparib in water with time, including for the physical mixture of olaparib amorphous and sulfobutylether-β-cyclodextrin, the physical mixture of olaparib crystal and sulfobutylether-β-cyclodextrin, and the olaparib amorphous and sulfobutylether-β-cyclodextrin inclusion complex. The data shown in FIG. 4 demonstrate that the dissolution of the olaparib-sulfobutylether-β-cyclodextrin inclusion complex in water was complete in almost 2 min. While, for the physical mixture of olaparib amorphous and sulfobutylether-β-cyclodextrin, the maximum dissolution yield was only around 80% after 10 min, meaning approximately 20% was not dissolved. Furthermore, the physical mixture of the olaparib crystals and sulfobutylether-β-cyclodextrin only reached 30% dissolution after 10 min.

Example 4

Figure 5:
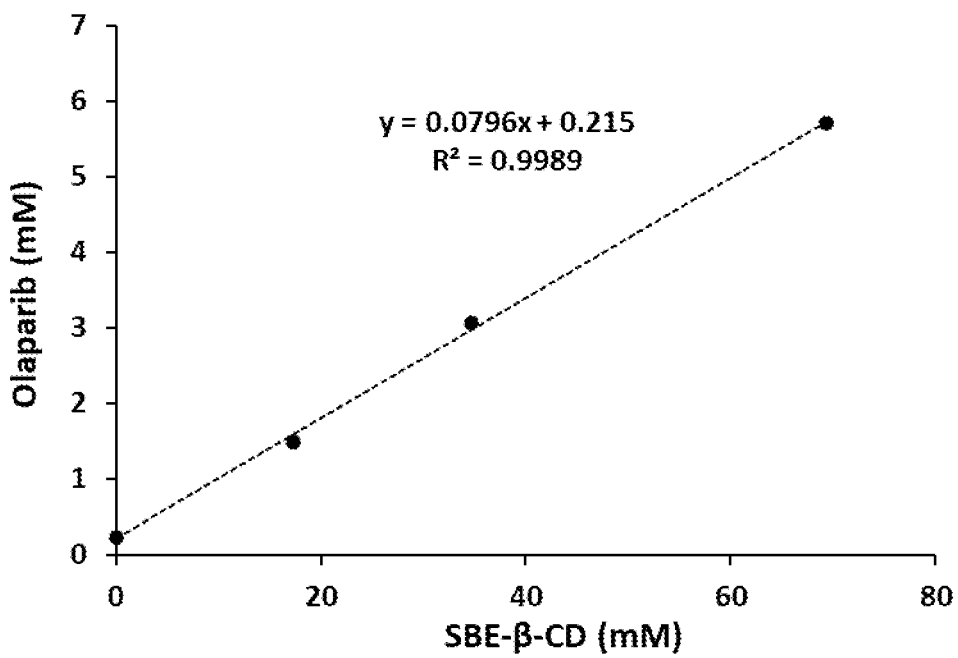
FIG. 5 shows an olaparib-sulfobutylether-β-cyclodextrin phase solubility diagram at 22° C.

Phase Solubility of Sulfobutylether-β-Cyclodextrin Inclusion Complex of Olaparib Sulfobutylether-β-cyclodextrin-enabled olaparib solubility enhancement experiments were conducted at various olaparib and sulfobutylether-β-cyclodextrin concentrations (FIG. 5). The dissolved quantity of olaparib increased when the concentration of sulfobutylether-β-cyclodextrin increased, indicating the formation of a 1:1 complex between the drug and solubilizer. The apparent complexation constant (K1:1) was calculated to be 432.4 $M^{-1}$ at 22° C.

These experiments suggested that to achieve 5 mg/ml olaparib (i.e., 0.01149 M) concentration, a minimum of 224 mg/mL (0.1036 M) sulfobutylether-β-cyclodextrin was needed. This would be equivalent to >10 and >50 molar and weight ratios, respectively. Solubility studies of 1:10 and 1:12 molar ratios of olaparib-sulfobutylether-β-cyclodextrin formulations showed full recovery of the olaparib, demonstrating that sulfobutylether-β-cyclodextrin enhances the solubility significantly.

Sulfobutylether-β-cyclodextrin solutions with 9.5% to 11.5% (w/v) are iso-osmotic with blood and extracellular fluid. However, direct injection of 30-40% (w/v) did not lead to any hypertonicity-related adverse effects in preclinical studies, suggesting the feasibility of IV administration of olaparib formulations with sulfobutylether-β-cyclodextrin concentration of 250 mg/ml (i.e., 25% w/v).

Example 5

Figure 6:
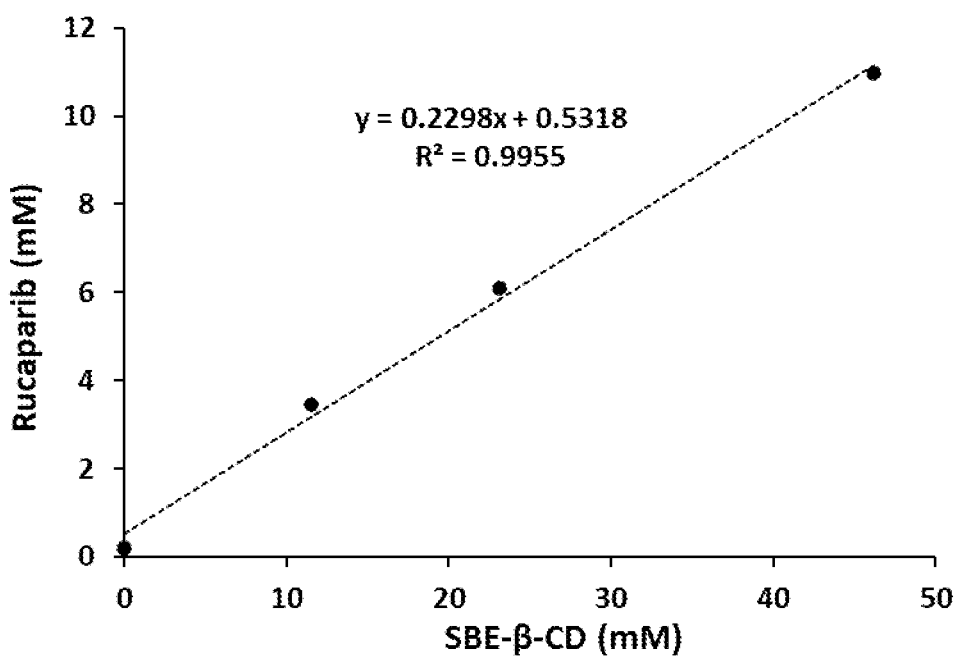
FIG. 6 shows a rucaparib-sulfobutylether-β-cyclodextrin phase solubility diagram at 22° C.

Phase Solubility of Sulfobutylether-β-Cyclodextrin Inclusion Complex of Rucaparib Sulfobutylether-β-cyclodextrin-enabled rucaparib solubility enhancement experiments were conducted at various rucaparib and sulfobutylether-β-cyclodextrin concentrations (FIG. 6). The dissolved quantity of rucaparib increased when the concentration of sulfobutylether-β-cyclodextrin increased, indicating the formation of a 1:1 complex between the drug and solubilizer. The apparent complexation constant (K1:1) was calculated to be 596.7 $M^{-1}$ at 22° C.

Example 6

Stability of Lyophilized Powder Injectable Formulation of Olaparib

Figure 7:
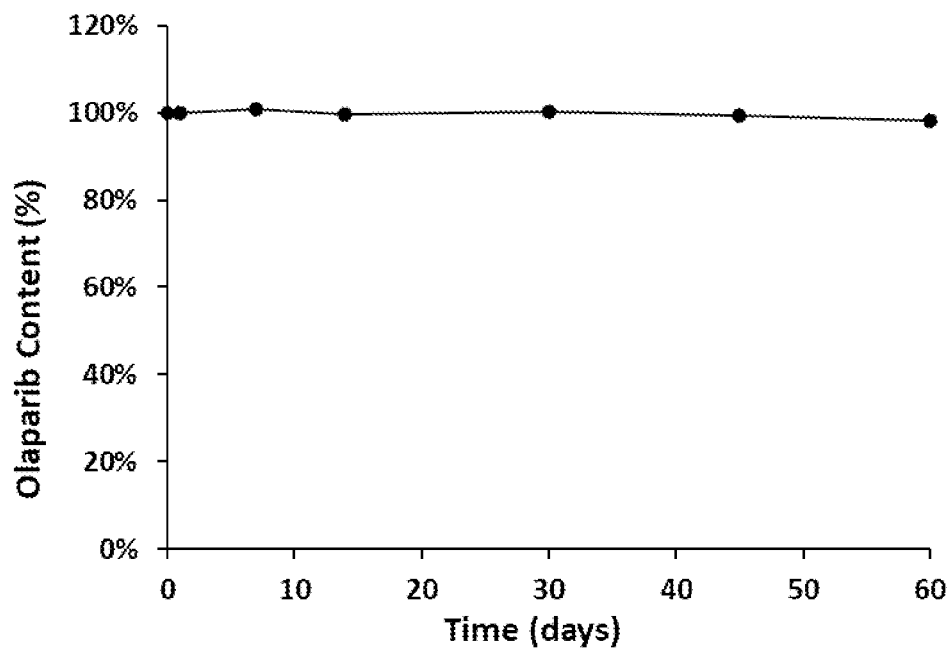
FIG. 7 shows the change of olaparib content (normalized to the initial sample) in the olaparib-sulfobutylether-β-cyclodextrin lyophilized powder after storage at 50° C., 15% relative humidity for 60 days.

A lyophilized powder of a 1:11 molar ratio of olaparib to sulfobutylether-β-cyclodextrin was prepared and tested under accelerated stability study conditions. For this purpose, the lyophilized powder samples were stored at 50° C./15% relative humidity (RH) for two months and tested on days 1, 7, 14, 30, 45, and 60. Olaparib amorphous powder alone (i.e., without sulfobutylether-β-cyclodextrin) was used as a control under similar storage conditions. FIG. 7 shows no significant degradation (<2%) of the lyophilized powder of olaparib formulation during this period, suggesting that the drug product is very stable under these conditions (50° C./15% RH). These results suggest that the shelf-life and stability of the olaparib-sulfobutylether-β-cyclodextrin lyophilized drug product could be about 3 years if stored at room temperature.

Example 7

Pharmacokinetics of Lyophilized Powder Injectable Formulation of Olaparib Following IV Administration in Normovolemic Swine A pharmacokinetic (PK) study was conducted in a normovolemic swine model with IV administrations of a 1 mg/kg olaparib-sulfobutylether-β-cyclodextrin formulation. Formulations with ~10% (w/v) were used for IV administrations. Blood samples were collected at the following time points within 4 hours after the drug administration: immediately after the drug administration (0.5-1 min), 15 min, 30 min, 45 min, 1 hr, 1.5 hr, 2 hr, 3 hr, and 4 hr.

Figure 8:
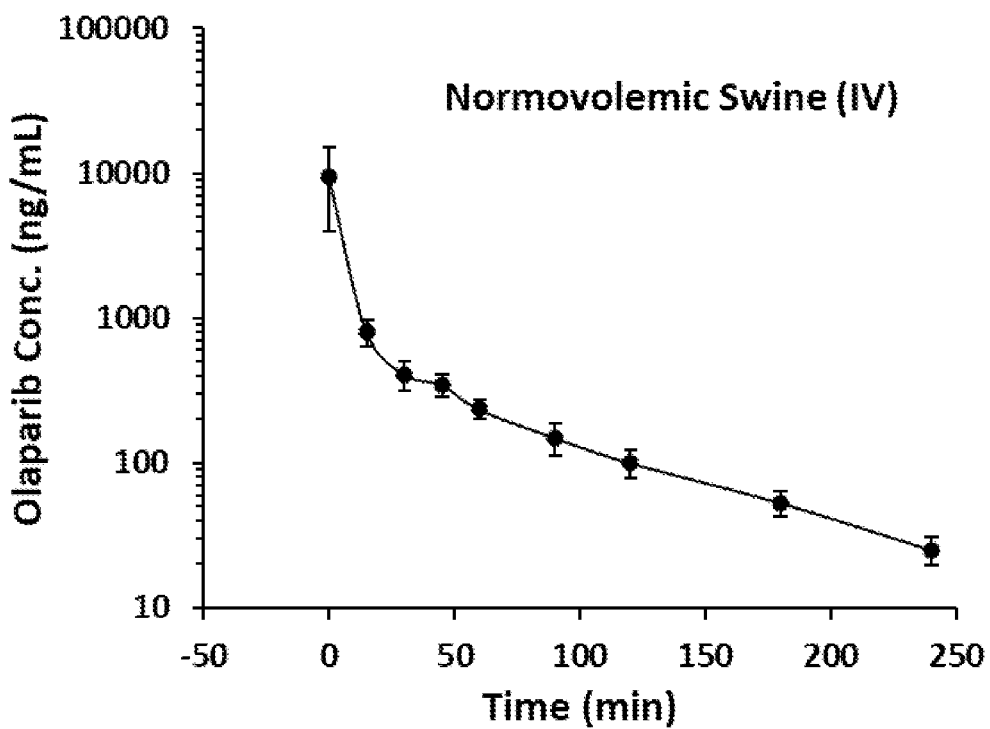
FIG. 8 shows the plasma concentration of olaparib as a function of time following intravenous (IV) administration of a 1 mg/kg olaparib-sulfobutylether-β-cyclodextrin formulation in normovolemic swine (n=5).

FIG. 8 shows the plasma concentration of olaparib formulation after IV administrations in normovolemic swine. The drug concentrations were around 10 μg/mL immediately after IV administration. Subsequently, the drug concentration decreased rapidly, i.e., the drug concentrations reduced to <1 μg/mL 15 min after the administration. This could be attributed to the perfusion-caused drug distribution in tissues.

Example 8

Pharmacokinetics of Lyophilized Powder Injectable Formulation of Olaparib Following IV Administration in Hypovolemic Swine Model A pharmacokinetic (PK) study was conducted in a hypovolemic swine model (with 35% blood loss) with IV administrations of a 1 mg/kg olaparib-sulfobutylether-β-cyclodextrin formulation. Formulations with ~10% (w/v) were used for IV administrations. Blood samples were collected at the following time points within 4 hours after the drug administration: immediately after the drug administration (0.5-1 min), 15 min, 30 min, 45 min, 1 hr, 1.5 hr, 2 hr, 3 hr, and 4 hr.

Figure 9:
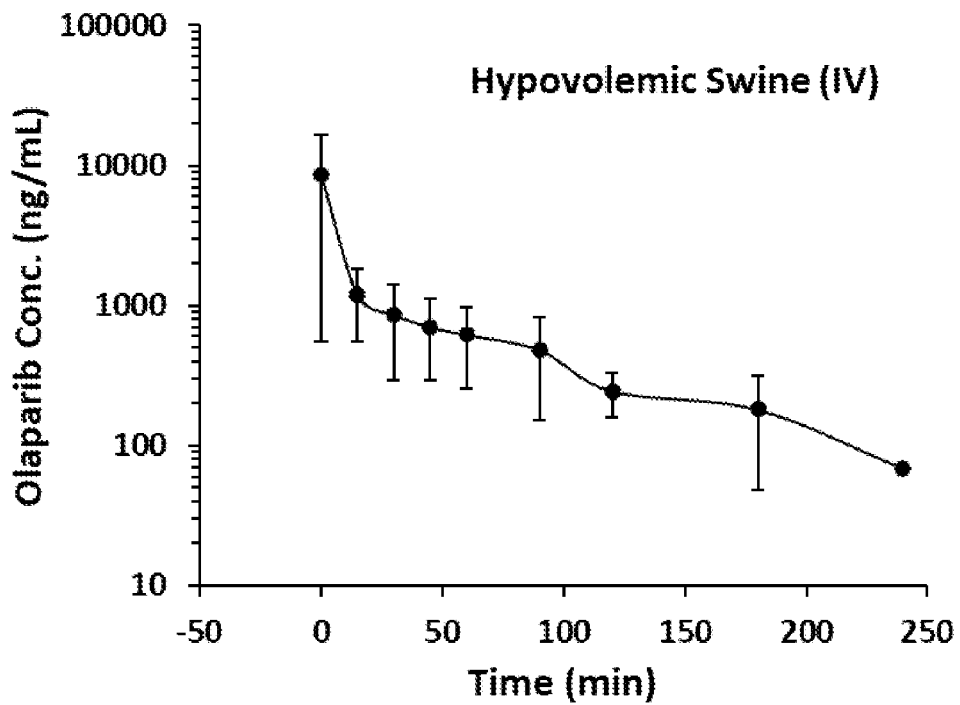
FIG. 9 shows the plasma concentration of olaparib as a function of time following intravenous (IV) administration of a 1 mg/kg olaparib-sulfobutylether-β-cyclodextrin formulation in hypovolemic swine (n=5).

FIG. 9 shows the plasma concentration of olaparib formulation after IV administration. The drug concentrations were around 10 μg/mL immediately after IV administration. Subsequently, the drug concentration decreased rapidly, i.e., the drug concentrations reduced to <1 μg/mL approximately 20 min after the administration. This could be attributed to the perfusion-caused drug distribution in tissues.

Example 9

Pharmacokinetics of Lyophilized Powder Injectable Formulation of Olaparib Following IM Administration A pharmacokinetic (PK) study was conducted in a normovolemic swine model with IM administrations of a 1 mg/kg olaparib in the form of olaparib-sulfobutylether-β-cyclodextrin aqueous formulation of 28% (w/v). Blood samples were collected at the following time points within 4 hours after the drug administration: immediately after the drug administration (0.5-1 min), 15 min, 30 min, 45 min, 1 hr, 1.5 hr, 2 hr, 3 hr, and 4 hr.

Figure 10:
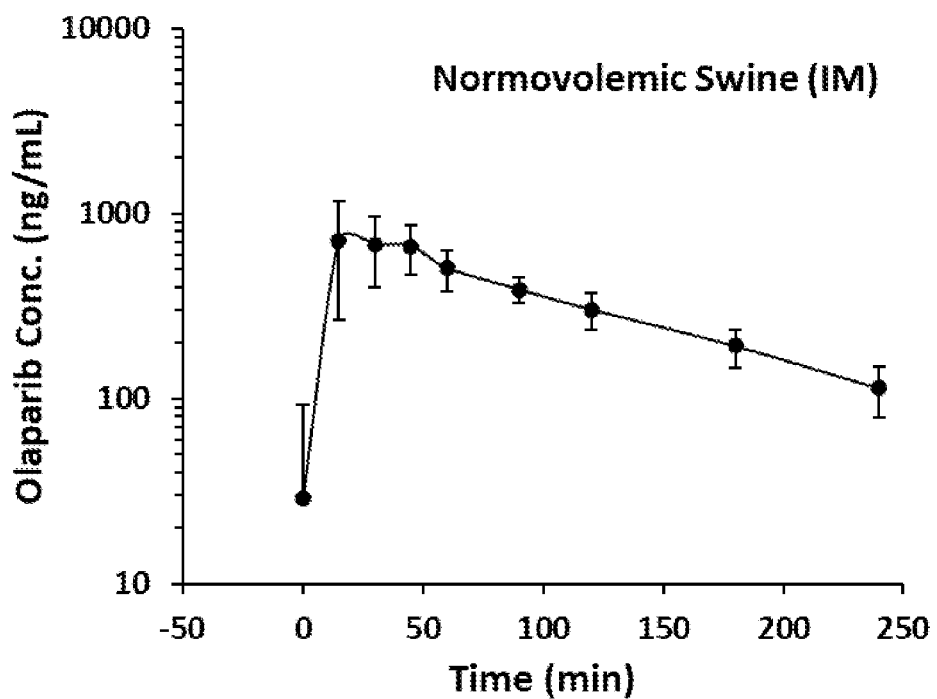
FIG. 10 shows the plasma concentration of olaparib as a function of time following intramuscular (IM) administration of a 1 mg/kg olaparib-sulfobutylether-β-cyclodextrin formulation in normovolemic swine (n=5).

The peak plasma concentration of olaparib reached ~800 ng/ml 15 min post-IM administration (FIG. 10). The plasma concentrations were maintained at this level until 45 min, followed by a steady decrease to <100 ng/ml (at 4 h). The olaparib AUC (within 4 hours) in the normovolemic IM group was determined to be 75.8% of the normovolemic IV group, indicating that the majority of the drug molecules were absorbed from the intramuscular injection site to the blood circulation with normal tissue perfusion.

Example 10

Comparison of PK Parameters for Injectable Formulation and Oral Formulation of Olaparib A comparison was made between the PK parameters of an injected olaparib-sulfobutylether-β-cyclodextrin pharmaceutical composition in a swine model and an olaparib 300 mg oral tablet formulation in humans (Table 3). The $T_{max}$ and clearance time of the olaparib-sulfobutylether-β-cyclodextrin with IV administration were <1 minute and 1 hr, respectively. On the other hand, the $T_{max}$ and $T_{1/2}$ of the oral olaparib formulation in humans were 1.5 hr and 15 hr, respectively.

TABLE 3

Pharmacokinetic Parameters for Injectable and Oral Olaparib Formulations

| Administration Route | $T_{max}$ (min) | $T_{1/2}$ (min) |
| --- | --- | --- |
| Intravenous (swine) | <1 | ~60 |
| Intramuscular (swine) | 15 | ~120 |
| Oral (human) | 90 | 900 |

Example 11

Olaparib Solubility with β-Cyclodextrin and D-Mannitol Excipients

To test the solubility enhancement of olaparib using β-cyclodextrin and D-mannitol, a saturated solution of each excipient was made. The saturated water solubility of β-cyclodextrin and D-mannitol are 0.7 mM (18.5 mg/mL) and 0.06 mM (216 mg/mL) at 25° C., respectively. 2.5 mL solutions of each excipient with each concentration were prepared by serial dilution of the saturated solution. One vial for each excipient experiment was prepared with 2.5 ml water. To each vial, 50 mg olaparib was added, sonicated, vortexed, and shaken at 40° C. for over 20 hr. After agitation at 25° C., the suspensions were filtered to obtain clear solutions. The clear solutions were analyzed using HPLC.

Figure 11A:
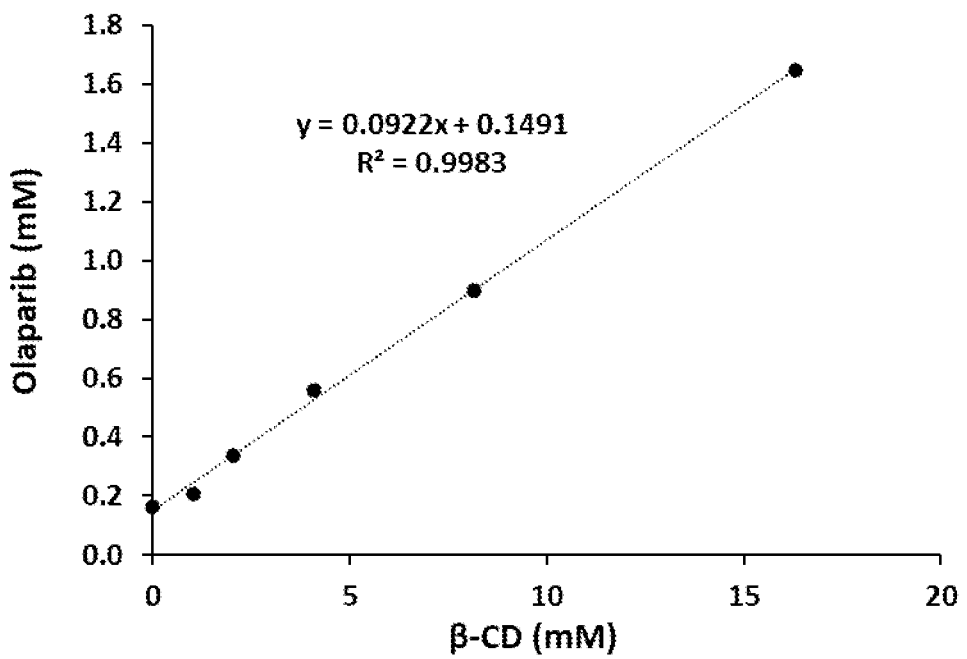
FIG. 11A-B show olaparib/excipient solubility plots.
Figure 11B:
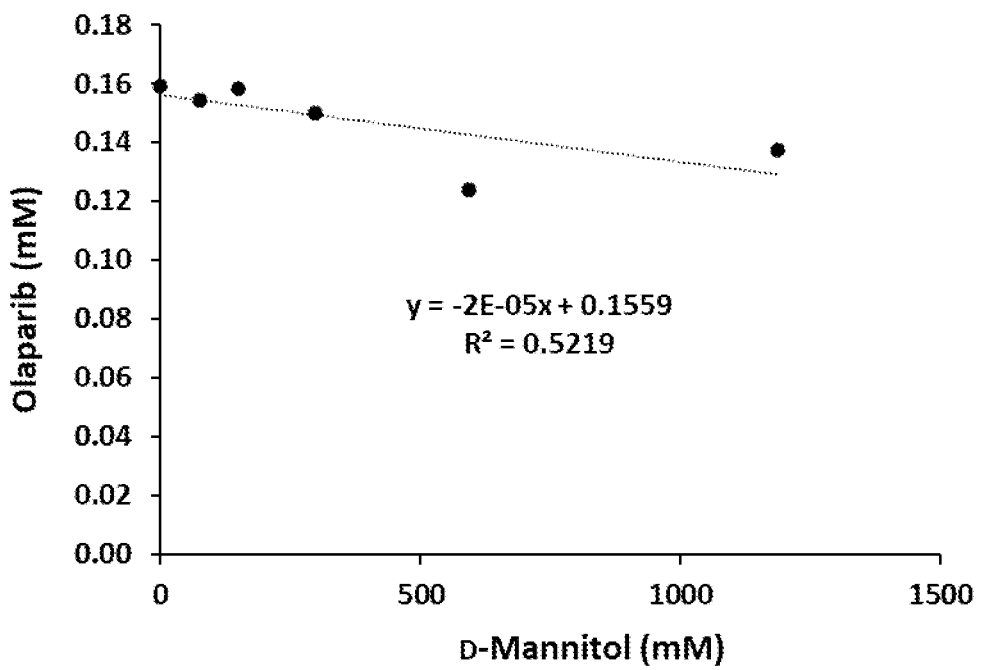

FIG. 11A and FIG. 11B show phase solubility diagrams for β-cyclodextrin and D-mannitol, respectively. The test results show that the solubility of olaparib increased to 1.65 mM (0.7 mg/mL) with 16 mM (18.5 mg/mL) β-cyclodextrin solution. D-mannitol did not enhance olaparib solubility.

Example 12

Olaparib Solubility with 2-Hydroxypropyl-Cyclodextrin Excipients

Figure 12A:
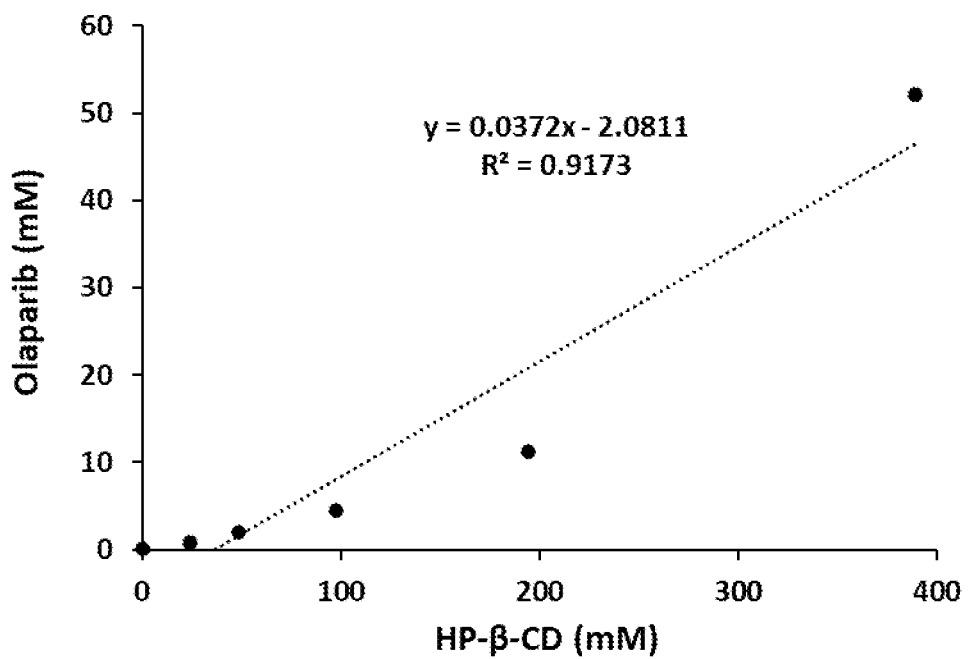
FIG. 12A-B show olaparib/hydroxypropyl (HP)-cyclodextrin solubility plots.
Figure 12B:
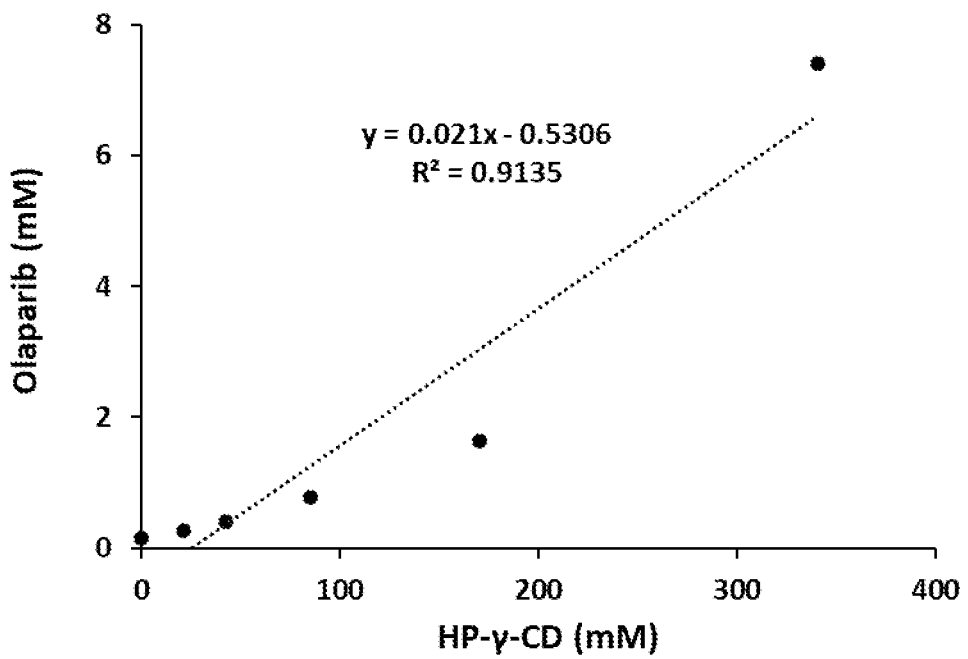

For solubility enhancement of olaparib by 2-hydroxypropyl-β-cyclodextrin (HP-β-cyclodextrin) and hydroxypropyl-γ-cyclodextrin (HP-γ-cyclodextrin), a 600 mg/mL solution of each excipient was made. 2.5 mL solutions of each excipient with each concentration were prepared by serial dilution of the 600 mg/mL solution. One vial for each excipient experiment was prepared with 2.5 mL water. To each vial, 50 mg olaparib was added, sonicated, vortexed, and shaken at 40° C. for over 20 hours. After agitation at 25° C., the suspensions were filtered to obtain clear solutions. The clear solutions were analyzed using HPLC. FIG. 12A-B show phase solubility diagrams for HP-β-cyclodextrin and HP-γ-cyclodextrin. The test results show that the solubility of olaparib increased to 52 mM (22.7 mg/mL) with 600 mg/mL HP-β-cyclodextrin solution and increased to 7.4 mM (3.2 mg/mL) with 600 mg/mL HP-γ-cyclodextrin.

Example 13

Comparison of Olaparib Solubility with Different Solubilizing Excipients

Table 4 shows the olaparib solubility with five different sugar-based solubilizing excipients. The molecular masses used for the molarity calculations are: olaparib, 435.08 g/mol; sulfobutylether β-cyclodextrin, 2163 g/mol; HP-β-cyclodextrin, 1542 g/mol; HP-γ-cyclodextrin, 1762 g/mol; β-cyclodextrin, 1135 g/mol; and D-Mannitol, 182.17 g/mol. HP-β-cyclodextrin and sulfobutylether β-cyclodextrin significantly enhanced the olaparib solubility in water at 25° C. with more than 100-fold solubility improvement. Further, due to its large interior cavity, HP-γ-cyclodextrin only improved the water solubility of olaparib 46-fold. The monosaccharide sugar, D-mannitol, which is highly water soluble itself and is often used in many pharmaceutical compositions for drug solubility enhancement, failed to improve the olaparib solubility in water. In addition, due to its own low solubility, β-cyclodextrin only improved the water solubility of olaparib by 10-fold, which is not sufficient for some injection dosages.

TABLE 4

Olaparib Solubility with Excipients

| | Solubility (mg/mL, 25° C.) in Water | Olaparib Solubility with Excipient (25° C.) in Water | | Solubility Enhancement Factor |
|---|---|---|---|---|
| | mg/mL | mg/mL | mM | |
| Olaparib | ~0.07 | 0.07 | 0.16 | — |
| Sulfobutylether β-cyclodextrin | ~600 | 13.3 | 30.57 | 190 |
| HP-β-cyclodextrin | ~600 | 22.7 | 52.17 | 324 |
| HP-γ-cyclodextrin | ~600 | 3.2 | 7.35 | 46 |
| β-cyclodextrin | 18.5 | 0.7 | 1.61 | 10 |
| D-mannitol | 216 | ~0.07 | 0.38 | 1 |

What is claimed:

1. A pharmaceutical composition comprising an amorphous powder of an inclusion complex comprising olaparib and a cyclodextrin (CD) derivative comprising sulfobutylether-β-cyclodextrin (SBE-β-CD) in a mass ratio of olaparib to CD derivative of about 1:60 to about 1:1000.

2. The pharmaceutical composition of claim 1, wherein the pharmaceutical composition is stable for at least about 3 years at room temperature.

3. The pharmaceutical composition of claim 1, wherein the pharmaceutical composition completely dissolves in an aqueous solution in less than about 10 minutes.

4. A kit comprising:
the pharmaceutical composition of claim 1;
optionally, a diluent or solvent;
optionally, injection or infusion materials or devices; and
optionally, one or more of packaging, a label, or instructions for use.

5. A method of treating, ameliorating, or inhibiting the progress of hemorrhagic shock, septic shock, or ovarian, prostate, breast, or pancreatic cancer in a subject in need thereof, the method comprising:
dissolving the pharmaceutical composition of claim 1 with a pharmaceutically acceptable solution for injection or infusion; and
administering a therapeutically effective amount of the dissolved pharmaceutical composition to a subject in need thereof by injection or infusion.

6. The method of claim 5, wherein the dissolved pharmaceutical composition is free of organic solvents.

7. A method of treating, ameliorating, or inhibiting the progress of hemorrhagic shock, septic shock, or ovarian, prostate, breast, or pancreatic cancer in a subject in need thereof, the method comprising administering to the subject a therapeutically effective amount of a pharmaceutical composition comprising olaparib and a cyclodextrin (CD) derivative comprising sulfobutylether-β-cyclodextrin (SBE-β-CD) in an inclusion complex and in a mass ratio of olaparib to CD derivative of about 1:60 to about 1:1000.

8. The method of claim 7, wherein the pharmaceutical composition is administered to the subject by intravenous, intravascular, intraosseous, intraarterial, intramuscular, subcutaneous, or intraperitoneal injection or infusion.

9. The method of claim 7, wherein the therapeutically effective amount of the pharmaceutical composition is from about 0.05 mg/kg to about 1.0 mg/kg for hemorrhagic shock; from about 0.1 mg/kg to about 2.0 mg/kg for septic shock; and from about 0.3 mg/kg to about 2.7 mg/kg for ovarian, prostate, breast, or pancreatic cancer.

10. The method of claim 7, wherein the subject is a mammal selected from a human, horse, cow, pig, sheep, goat, rabbit, dog, or cat.

11. A method of making an amorphous powdered pharmaceutical composition, the method comprising:
mixing olaparib with an aqueous solution of a cyclodextrin (CD) derivative comprising sulfobutylether-β-cyclodextrin (SBE-β-CD) at a mass ratio of about 1:60 to about 1:1000 to create a mixture of the olaparib and the CD derivative in an inclusion complex;
freezing the mixture at −80° C.; and
lyophilizing the frozen mixture to create the amorphous powdered pharmaceutical composition.

12. The method of claim 11, wherein the olaparib is an amorphous powder form made by dissolving the olaparib in a solvent comprising an alcohol and water; freezing the solution at −80° C.; and lyophilizing the frozen solution to create the amorphous powder form of the olaparib.

13. The method of claim 11, wherein mixing further comprises one or more of adding water to the mixture, sonicating the mixture, agitating the mixture, or filtering the mixture.

14. An injectable or infusible pharmaceutical composition made by a process comprising:
   mixing olaparib with an aqueous solution of a cyclodextrin (CD) derivative comprising sulfobutylether-β-cyclodextrin (SBE-β-CD) at a mass ratio of about 1:60 to about 1:1000 to create a mixture of the olaparib and the CD derivative in an inclusion complex;
   freezing the mixture at −80° C.;
   lyophilizing the frozen mixture to create an amorphous powdered pharmaceutical composition; and
   dissolving the amorphous powdered pharmaceutical composition with a pharmaceutically acceptable solution for injection or infusion.

\* \* \* \* \*